(12) United States Patent
Gerlach

(10) Patent No.: US 10,278,809 B2
(45) Date of Patent: May 7, 2019

(54) MULTIFOCAL EYE LENS HAVING OPTICAL ZONES WHICH AT LEAST PARTLY ENCIRCLE A MAIN OPTICAL AXIS

(71) Applicant: Carl Zeiss Meditec AG, Jena (DE)

(72) Inventor: Mario Gerlach, Glienicke-Nordbahn (DE)

(73) Assignee: Carl Zeiss Meditec AG, Jena (DE)

( * ) Notice: Subject to any disclaimer, the term of this patent is extended or adjusted under 35 U.S.C. 154(b) by 139 days.

(21) Appl. No.: 15/045,103

(22) Filed: Feb. 16, 2016

(65) Prior Publication Data

US 2016/0220350 A1  Aug. 4, 2016

Related U.S. Application Data

(63) Continuation of application No. PCT/EP2014/066704, filed on Aug. 4, 2014.

(30) Foreign Application Priority Data

Aug. 13, 2013  (DE) .................. 10 2013 216 015

(51) Int. Cl.
| | | |
|---|---|---|
| *A61F 2/16* | (2006.01) | |
| *G02B 27/00* | (2006.01) | |
| *G02C 7/04* | (2006.01) | |

(52) U.S. Cl.
CPC .......... *A61F 2/1618* (2013.01); *A61F 2/1624* (2013.01); *G02B 27/0075* (2013.01); *G02C 7/042* (2013.01); *A61F 2/1645* (2015.04); *A61F 2230/0006* (2013.01); *A61F 2250/0053* (2013.01)

(58) Field of Classification Search
CPC .... A61F 2/1618; A61F 2/1613; A61F 2/1645; A61F 2300/0006; G02B 27/0075; G02C 7/042
See application file for complete search history.

(56) References Cited

U.S. PATENT DOCUMENTS

| | | |
|---|---|---|
| 6,536,899 B1 | 3/2003 | Fiala |
| 8,465,543 B2 | 6/2013 | Fiala et al. |
| 8,500,805 B2 | 8/2013 | Kobayashi et al. |
| 9,223,148 B2 | 12/2015 | Fiala et al. |
| 2009/0164008 A1 | 6/2009 | Hong et al. |
| 2013/0138208 A1 | 5/2013 | Simonov et al. |
| 2014/0211313 A1* | 7/2014 | Dobschal ........... G02B 27/0075 359/569 |

(Continued)

OTHER PUBLICATIONS

Patent Examination Report of Australian Patent Office dated Jul. 15, 2016 in patent application 2014308014.

(Continued)

*Primary Examiner* — David H Willse
*Assistant Examiner* — Tiffany P Shipmon
(74) *Attorney, Agent, or Firm* — Walter Ottesen, P.A.

(57) ABSTRACT

A multifocal eye lenses including an optical part, which has a first optical side and an opposite second optical side viewed in the direction of a main optical axis (A) of the eye lens, and which has a plurality of annular optical zones that at least partly encircle the main optical axis (A) and are formed on at least one side, and zones each have at least one main sub-zone.

23 Claims, 37 Drawing Sheets

(56) References Cited

U.S. PATENT DOCUMENTS

2014/0293426 A1  10/2014  Dobschal

OTHER PUBLICATIONS

International preliminary report on patentability and written opinion of the international searching authority dated Feb. 16, 2016 in international patent application PCT/EP2014/066704 on which the claim of priority is based.
International Search Report dated Jan. 16, 2015 in international patent application PCT/EP2014/066704 on which be claim of priority is based.

* cited by examiner

FIG. 2A
```
P0    =  20;
add   =  3.75;
n1    =  1.336;
n2    =  1.46;
ct    =  0.001;
λ     =  0.546;
Δλ    =  0.46;
k     =  -2.75;
frac  =  0.85;
rm    =  3;
smax  =  nring[Padd];
cyl   =  0.0;
sph   =  20.0;
edof  =  1.0;
HOA1  =  0.0;
HOA2  =  0.0;
```
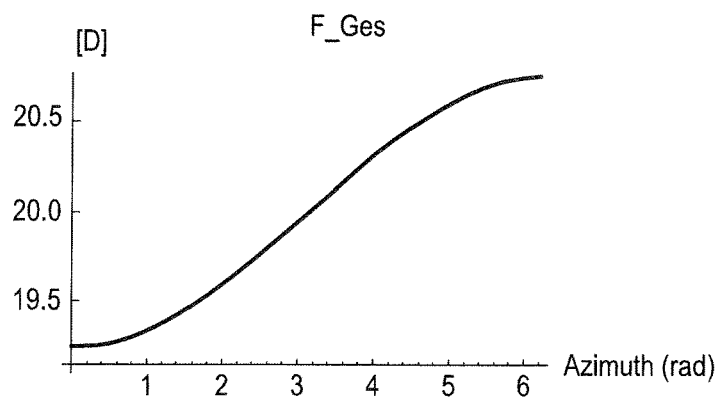
FIG. 2B
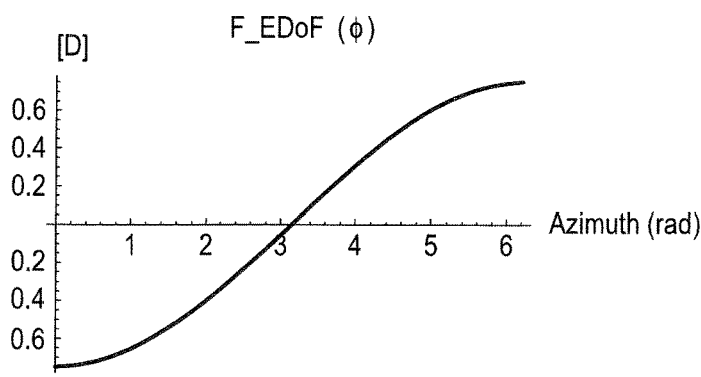
FIG. 2C

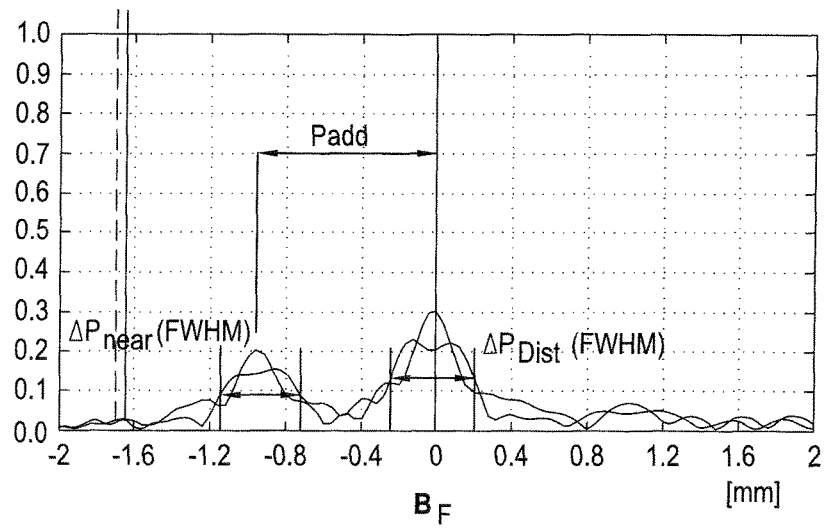
FIG. 2G
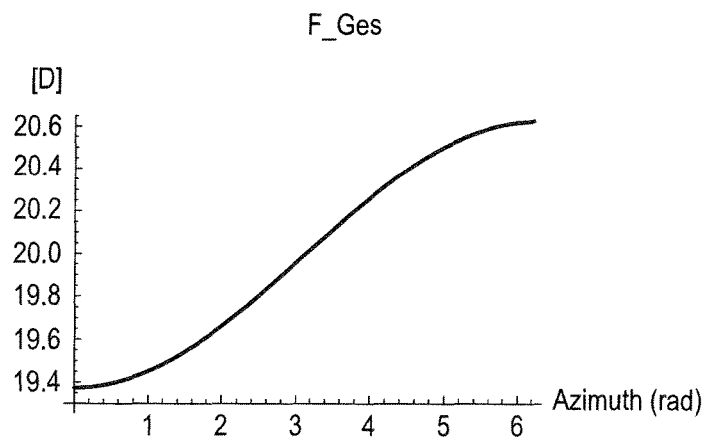
FIG. 3B
```
P0    =  20;
add   =  2.0;
n1    =  1.336;
n2    =  1.46;
ct    =  0.001;
λ     =  0.546;
Δλ    =  0.46;
k     =  -2.75;
frac  =  0.85;
rm    =  3;
smax  =  nring[Padd];
cyl   =  0.0;
sph   =  20.0;
edof  =  1.25;
HOA1  =  0.0;
HOA2  =  0.0;
```
FIG. 3A FIG. 4A
```
P0    =  20;
add   =  3.75;
n1    =  1.336;
n2    =  1.46;
ct    =  0.001;
λ     =  0.546;
Δλ    =  0.46;
k     =  -2.75;
frac  =  0.85;
rm    =  3;
smax  =  nring[Padd];
cyl   =  4.0;
sph   =  20.0;
edof  =  1.0;
HOA1  =  0.0;
HOA2  =  0.0;
```
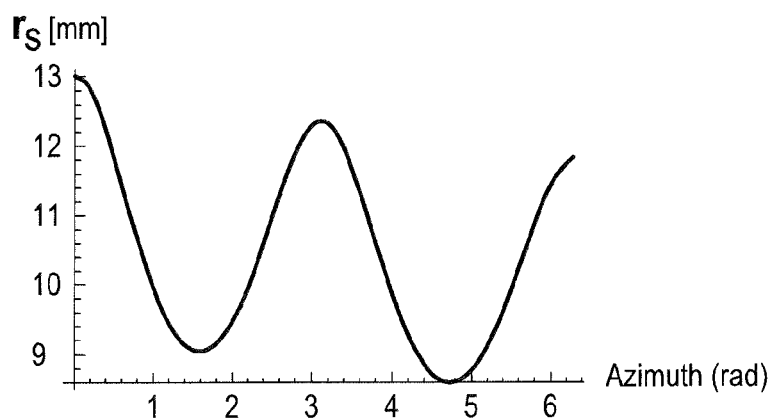
FIG. 4B
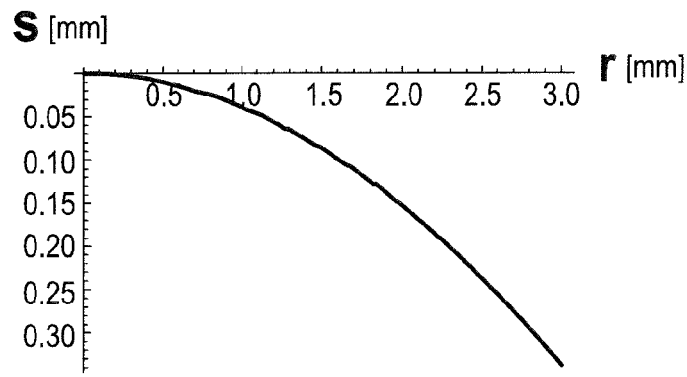
FIG. 4C FIG. 5A
```
P0    =  20;
add   =  2.0;
n1    =  1.336;
n2    =  1.46;
ct    =  0.001;
λ     =  0.546;
Δλ    =  0.46;
k     =  -2.75;
frac  =  0.85;
rm    =  3;
smax  =  nring[Padd];
cyl   =  4.0;
sph   =  20.0;
edof  =  0.0;
HOA1  =  0.0;
HOA2  =  0.0;
```
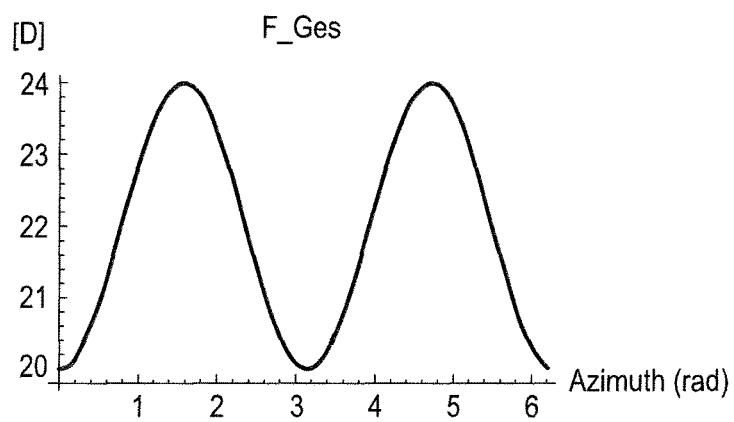
FIG. 5B
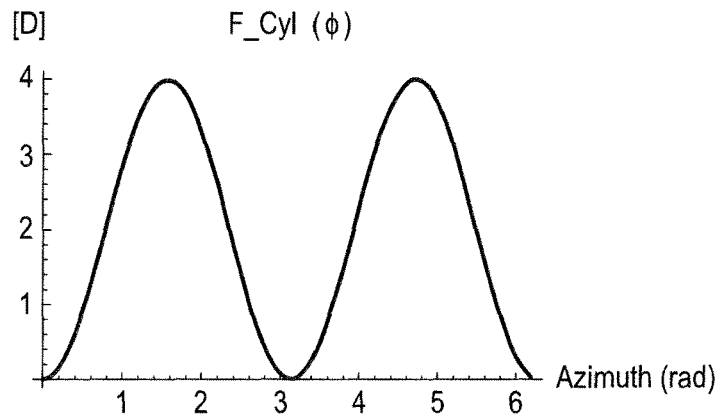
FIG. 5C

```
P0        =  5;
add       =  3.75;
n1        =  1.336;
n2        =  1.46;
ct        =  0.001;
λ         =  0.546;
k         =  -2.75;
frac      =  0.85;
rm        =  3;
smax      =  nring[Padd];
cyl       =  0.0;
sph       =  5.0;
edof      =  0.0;
HOA1      =  0.0;
HOA2      =  0.0;
phasemin  =  0.0;
phasemax  =  0.6;
rmmin     =  3.0;
rmmax     =  3.0;
```
FIG. 6A
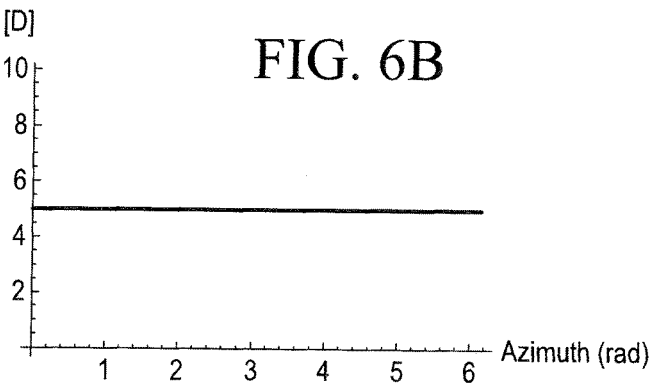
FIG. 6B
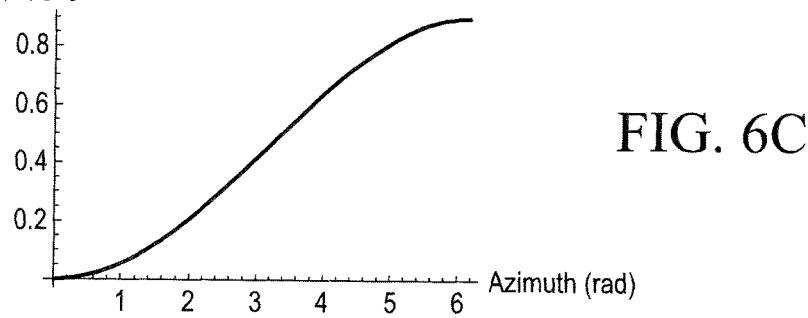
FIG. 6C
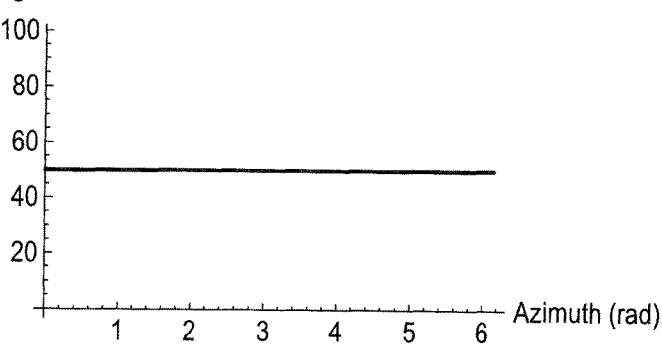
FIG. 6D FIG. 7A
| | | |
|---|---|---|
| P0 | = | 10; |
| add | = | 3.75; |
| n1 | = | 1.336; |
| n2 | = | 1.46; |
| ct | = | 0.001; |
| λ | = | 0.546; |
| k | = | -2.75; |
| frac | = | 0.85; |
| rm | = | 3; |
| smax | = | nring[Padd]; |
| cyl | = | 0.0; |
| sph | = | 10.0; |
| edof | = | 0.0; |
| HOA1 | = | 0.0; |
| HOA2 | = | 0.0; |
| phasemin | = | 0.45; |
| phasemax | = | 0.46; |
| rmmin | = | 3.0; |
| rmmax | = | 5.0; |
FIG. 7B
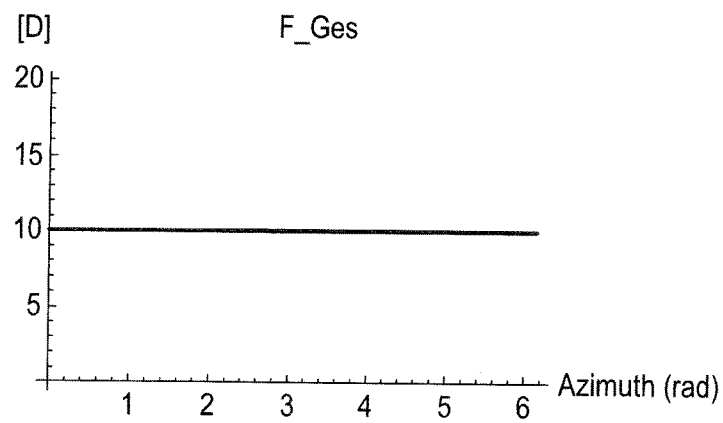
FIG. 7C
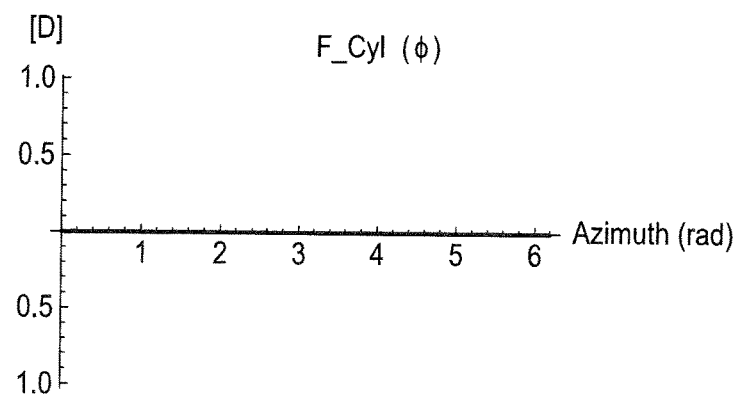

FIG. 8A
```
P0       = 5;
add      = 3.75;
n1       = 1.336;
n2       = 1.46;
ct       = 0.001;
λ        = 0.546;
Δλ       = 0.46;
k        = -2.75;
frac     = 0.85;
rm       = 3;
smax     = nring[Padd];
cyl      = 0.0;
sph      = 5.0;
edof     = 0.0;
HOA1     = 0.0;
HOA2     = 0.0;
phasemin = 0.0;
phasemax = 1.0;
rmmin    = 3.0;
rmmax    = 3.0;
```
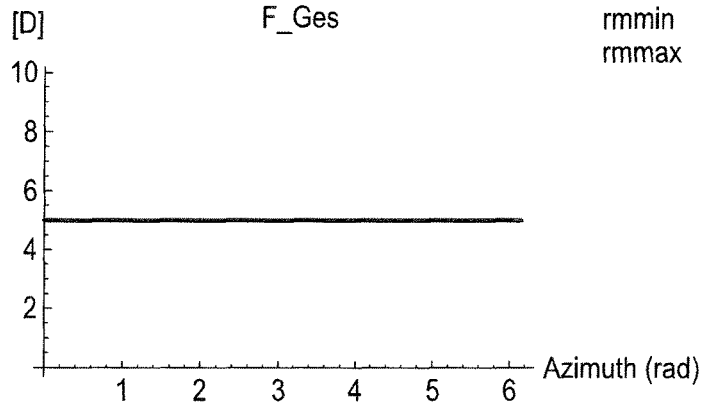
FIG. 8B
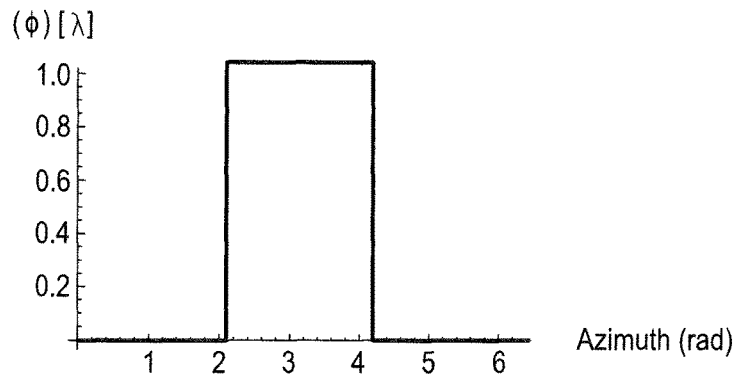
FIG. 8C FIG. 9A
```
P0       =   20;
add      =   3.75;
n1       =   1.336;
n2       =   1.46;
ct       =   0.001;
λ        =   0.546;
Δλ       =   0.46;
k        =   -2.75;
frac     =   0.85;
rm       =   3;
smax     =   nring[Padd];
cyl      =   4.0;
sph      =   20.0;
edof     =   0.0;
HOA1     =   0.0;
HOA2     =   0.0;
phasemin =   0.0;
phasemax =   1.0;
rmmin    =   3.0;
rmmax    =   3.0;
```
FIG. 9B
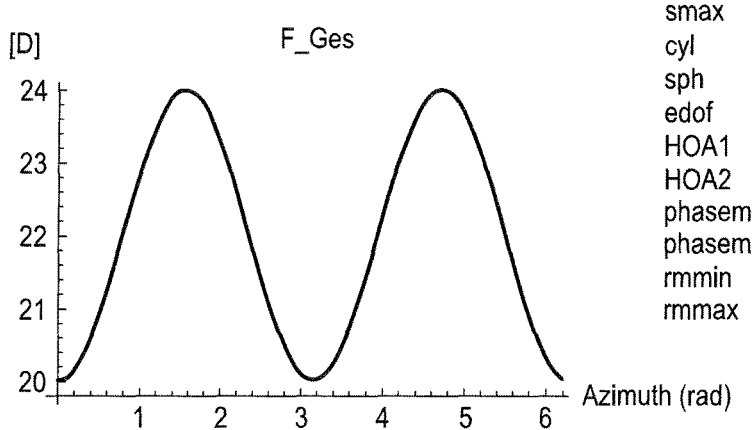
FIG. 9C
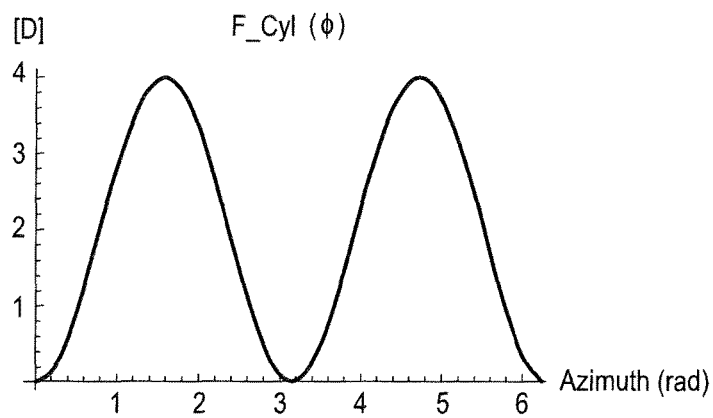
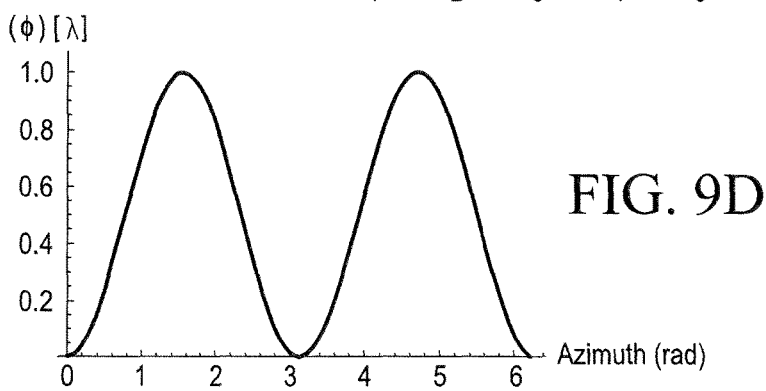
FIG. 9D FIG. 10A
| | | |
|---|---|---|
| P0 | = | 20; |
| add | = | 3.75; |
| n1 | = | 1.336; |
| n2 | = | 1.46; |
| ct | = | 0.001; |
| λ | = | 0.546; |
| Δλ | = | 0.46; |
| k | = | -2.75; |
| frac | = | 0.85; |
| rm | = | 3; |
| smax | = | nring[Padd]; |
| cyl | = | 2.0; |
| sph | = | 20.0; |
| edof | = | 0.0; |
| HOA1 | = | 0.0; |
| HOA2 | = | 0.0; |
| phasemin | = | 0.45; |
| phasemax | = | 0.46; |
| rmmin | = | 3.0; |
| rmmax | = | 4.5; |
FIG. 10B
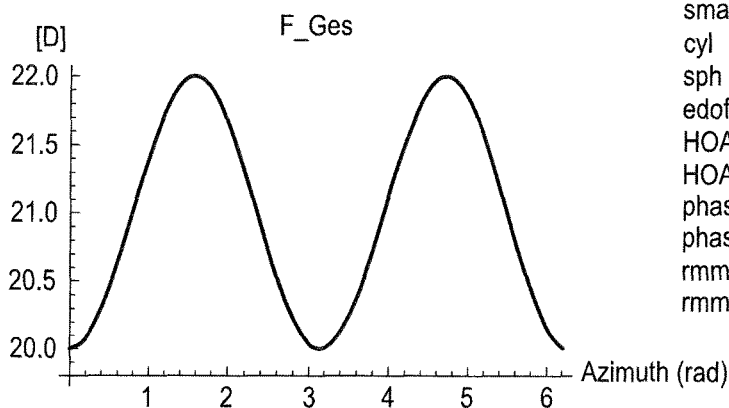
FIG. 10C
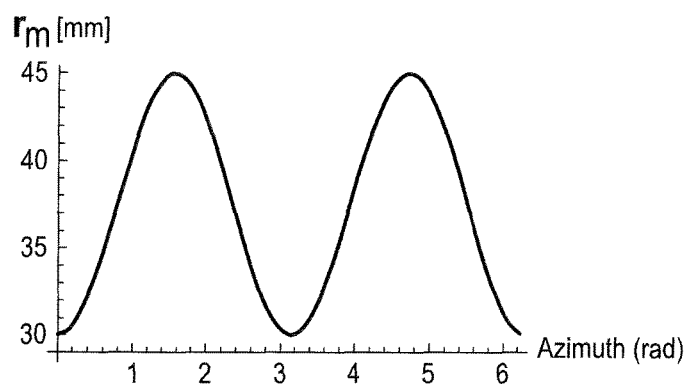
FIG. 10D
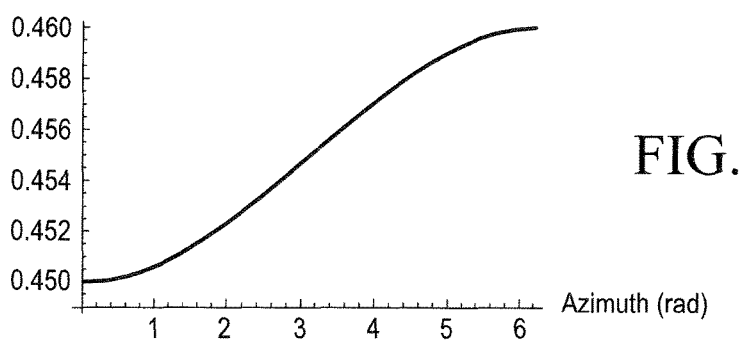

FIG. 11A
| | | |
|---|---|---|
| P0 | = | 10; |
| add | = | 3.75; |
| n1 | = | 1.336; |
| n2 | = | 1.46; |
| ct | = | 0.001; |
| λ | = | 0.546; |
| k | = | -2.75; |
| frac | = | 0.85; |
| rm | = | 3; |
| smax | = | nring[Padd]; |
| cyl | = | 2.0; |
| sph | = | 10.0; |
| edof | = | 0.0; |
| HOA1 | = | 0.0; |
| HOA2 | = | 0.0; |
| phasemin | = | 0.45; |
| phasemax | = | 0.46; |
| rmmin | = | 3.0; |
| rmmax | = | 3.25; |
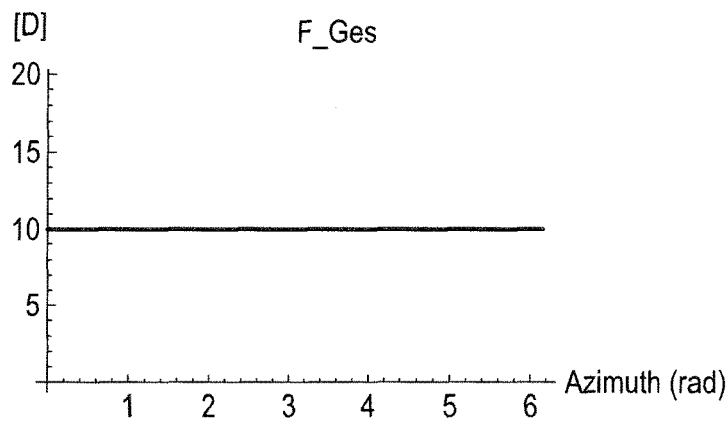
FIG. 11B
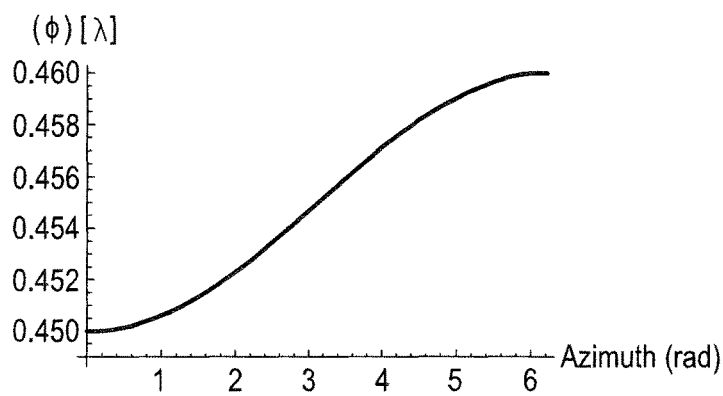
FIG. 11C

FIG. 12A
```
P0       =  10;
add      =  3.75;
n1       =  1.336;
n2       =  1.46;
ct       =  0.001;
λ        =  0.546;
k        =  -2.75;
frac     =  0.85;
rm       =  3;
smax     =  nring[Padd];
cyl      =  2.0;
sph      =  10.0;
edof     =  0.0;
HOA1     =  0.0;
HOA2     =  0.0;
phasemin =  0.45;
phasemax =  0.46;
rmmin    =  3.0;
rmmax    =  3.5;
```
FIG. 12B
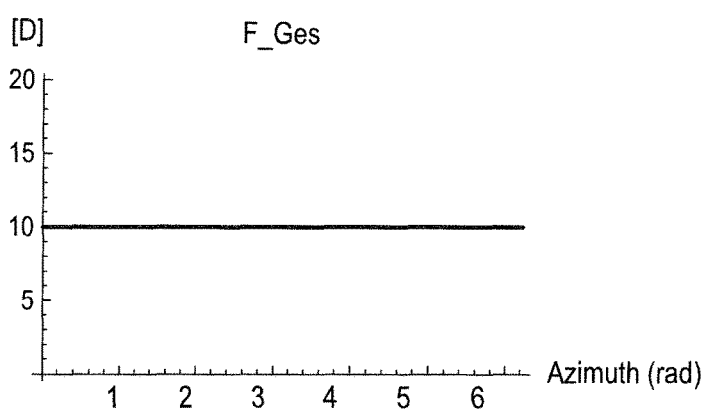
FIG. 12C
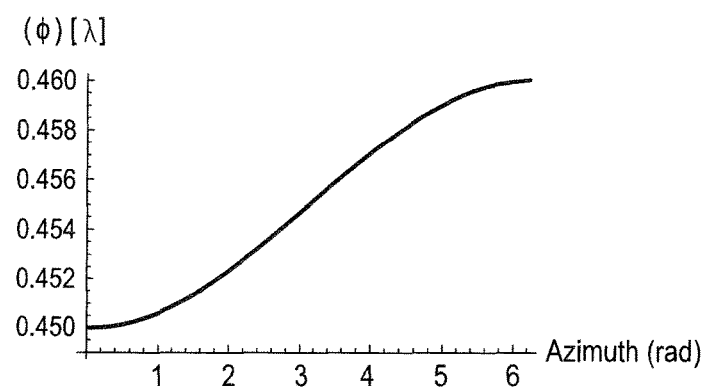
FIG. 12D
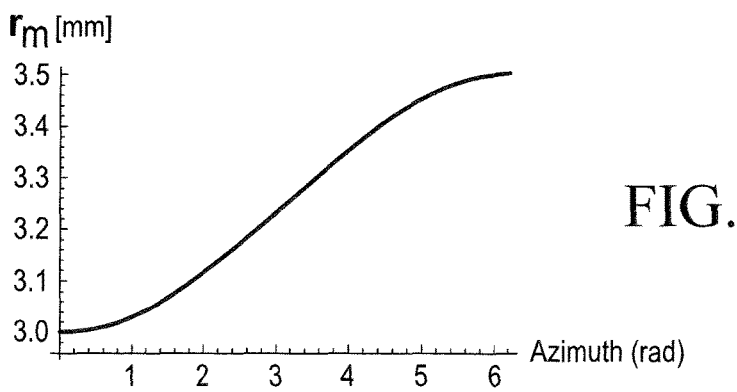

FIG. 13A
| | | |
|---|---|---|
| P0 | = | 10; |
| add | = | 3.75; |
| n1 | = | 1.336; |
| n2 | = | 1.46; |
| ct | = | 0.001; |
| λ | = | 0.546; |
| k | = | -2.75; |
| frac | = | 0.85; |
| rm | = | 3; |
| smax | = | nring[Padd]; |
| cyl | = | 2.0; |
| sph | = | 10.0; |
| edof | = | 0.0; |
| HOA1 | = | 0.0; |
| HOA2 | = | 0.0; |
| phasemin | = | 0.45; |
| phasemax | = | 0.46; |
| rmmin | = | 3.0; |
| rmmax | = | 3.75; |
FIG. 13B
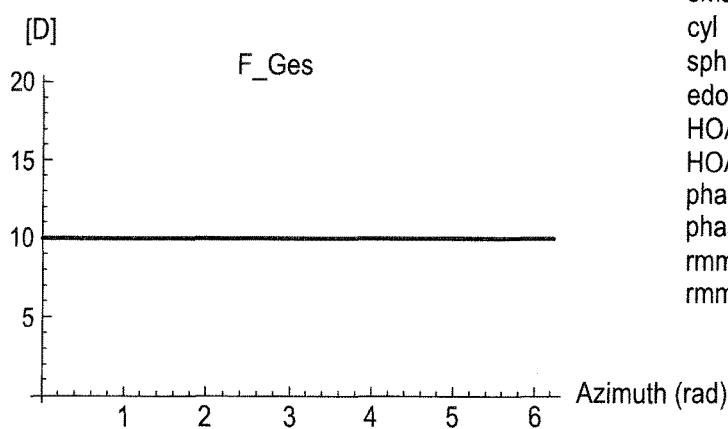
FIG. 13C
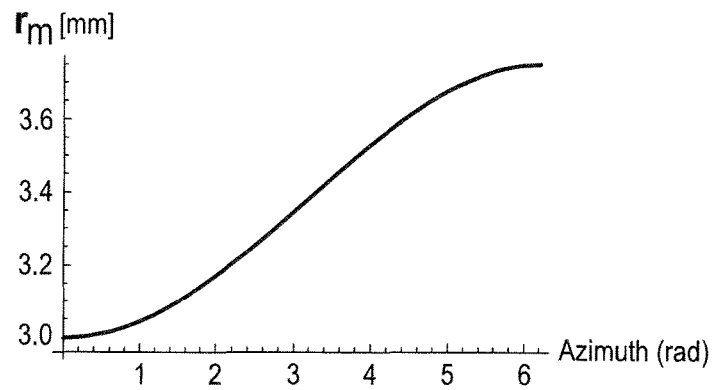
FIG. 13D
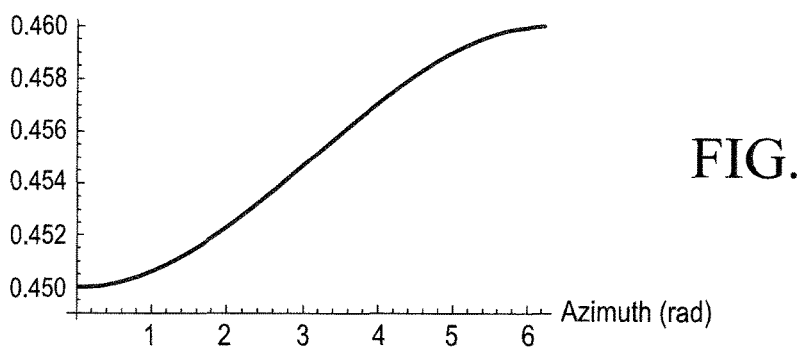

FIG. 14A
```
P0       =   10;
add      =   3.75;
n1       =   1.336;
n2       =   1.46;
ct       =   0.001;
λ        =   0.546;
k        =   -2.75;
frac     =   0.85;
rm       =   3;
smax     =   nring[Padd];
cyl      =   2.0;
sph      =   10.0;
edof     =   0.0;
HOA1     =   0.0;
HOA2     =   0.0;
phasemin =   0.45;
phasemax =   0.46;
rmmin    =   3.0;
rmmax    =   3.75;
```
FIG. 14B
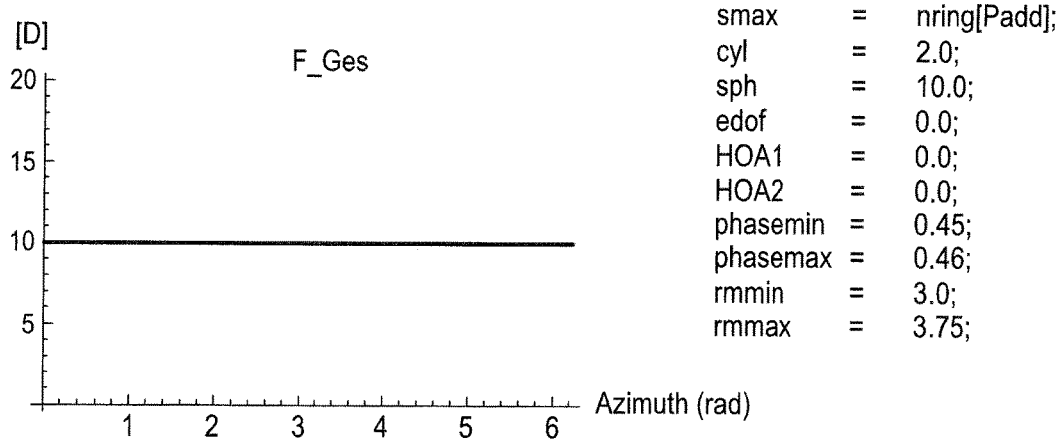
FIG. 14C
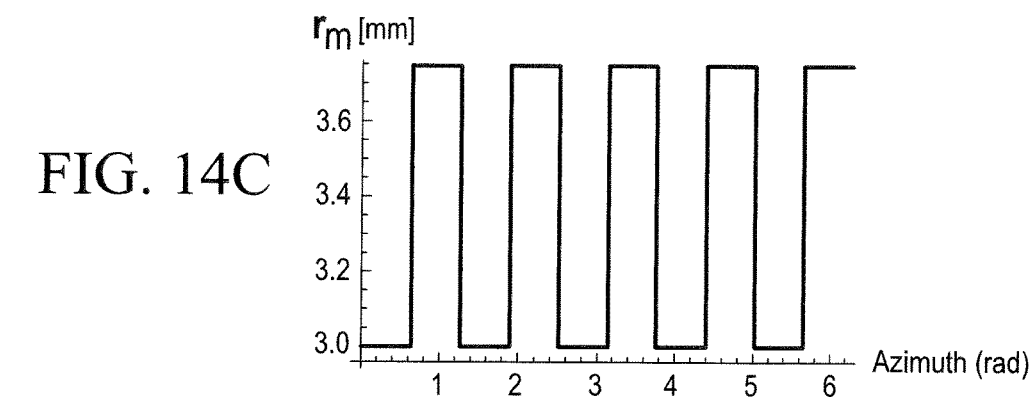
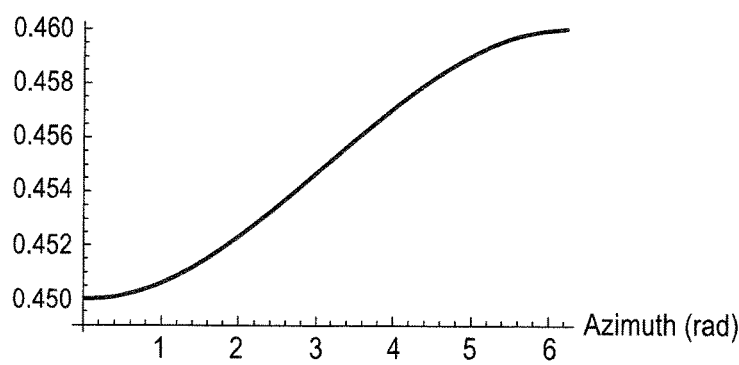
FIG. 14D

MULTIFOCAL EYE LENS HAVING OPTICAL ZONES WHICH AT LEAST PARTLY ENCIRCLE A MAIN OPTICAL AXIS

CROSS REFERENCE TO RELATED APPLICATIONS

This application is a continuation application of international patent application PCT/EP2014/066704, filed Aug. 4, 2014, designating the United States and claiming priority from German application 10 2013 216 015.1, filed Aug. 13, 2013, and the entire content of both applications is incorporated herein by reference.

FIELD OF THE INVENTION

The invention relates to multifocal eye lenses with an optical part having a first optical side and an opposite second optical side viewed in the direction of a main optical axis of the eye lens. The optical part of the multifocal eye lens includes a plurality of annular optical zones formed on at least one side, at least partly encircling the main optical axis, wherein zones each have at least one main sub-zone. A phase deviation is formed between two zones formed adjacent in radial direction and adjoining to each other.

BACKGROUND OF THE INVENTION

Multifocal lenses are known from U.S. Pat. No. 6,536,899. In the multifocal lenses there, it is provided that annular zones completely encircling the main optical axis are formed. Each zone has a main sub-zone and a phase sub-zone. A phase deviation is formed between two zones adjacent in radial direction. The zones have identical areas and an optical step is not formed between adjacent zones, which means that the surface configuration is continuous. In particular, this also means that a wave front behind the lens is continuous, that is that optical path length differences or optical steps do not occur between partial areas of the wave front behind the lens.

Interference problems, as they are also explained in the prior art, can be encountered by the phase sub-zones. Here, phase shifts between partial waves from different areas or zones of the lens, in which the phase shifts are requirements for multifocality of the lens, are not caused by optical steps as usual in diffractive lenses, but by these phase sub-zones with specific refractive power. Such a configuration and a corresponding construction of a lens with this division of annular zones into a main sub-zone and a phase sub-zone therefore present a basically different approach.

Moreover, from U.S. Pat. No. 9,223,148, a further configuration of a multifocal lens is known, in which the principle of the annular zones, of which zones have a main sub-zone and a phase sub-zone, is also shown.

As indicated in the prior art, the following relation applies to an averaged refractive power of the lens:

$$F_{AV} = (1-p)F_G + pF_S \quad (1)$$

wherein it applies therein that $F_{AV}$ is precisely the averaged refractive power, $F_G$ is a refractive power of a main sub-zone of a considered zone, $F_S$ is the refractive power in the phase sub-zone of this zone and p is the area portion of the main sub-zone of the entire zone.

Furthermore, the difference $\Delta F$ between the greater refractive power $F_2$ (near refractive power) and the smaller refractive power $F_1$ (far refractive power) also results from the addition refractive power of the at least bifocal lens formed of annular zones with respectively at least one main sub-zone and at least one phase zone as $$\Delta F = \frac{\lambda N}{B^2} \quad (2)$$

In this formula 2, $\lambda$ is the configuration wavelength, which can for example be between 540 and 560 nm, for example 546 nm. N is the number of the annular zones, and B is the diameter of the lens, on which the annular zones are located, and thus in particular the diameter of the optical part of the lens.

These known multifocal lenses have very good imaging characteristics.

From U.S. Pat. No. 8,465,543, an astigmatic intraocular lens is known, which therefore has a toric refractive lens surface.

Due to its relatively complex construction and thus in particular also the parts provided for optical imaging and/or other influencing factors, the human eye can be afflicted with very different visual defects. They can be individually differently pronounced in the intensity, on the other hand, a plurality of different visual defects can also be present in an eye.

In order to be able to at least substantially improve this visual defect complexity, it is a constant effort to further develop eye lenses to that effect. Especially in intraocular lenses, in this context, also with respect to the handling in a surgical procedure, the small incision capability and thus the introduction of a correspondingly folded intraocular lens through an incision in the eye as small as possible as well as the compactness of such a lens are also essential aspects, which are to be taken into account.

Considering all of these requirements, thus, corresponding operability requirements also have to be satisfied besides a plurality of optical requirements partly difficult to be dealt with.

SUMMARY OF THE INVENTION

It is an object of the present invention to provide a multifocal eye lens, which is further improved in its optical imaging characteristics.

This object is solved by a multifocal eye lens including: an optical part defining a main optical axis (A); said optical part, viewed in the direction of said main optical axis (A), having a first optical side and a second optical side disposed opposite to said first side; a plurality of annular optical zones formed on at least one of said first and said second side; said annular optical zones at least partially encircling said main optical axis (A); each of said annular optical zones including at least one main sub-zone; a helix winding formed on at least one of said first and said second side and configured, in addition to said annular optical zones, as surface structure of said optical part; said helix winding defining an encircling direction about said main axis (A); and, the lens having a refractive power varied via said helix winding in said circumferential direction.

According to a first aspect of the invention, a multifocal eye lens includes an optical part, which is characteristic to and responsible for the optical imaging characteristic of the eye lens. The optical part has a first optical side and an opposite second optical side viewed in the direction of a main optical axis of the eye lens. The first side can be the front side or the rear side of the optical part. Correspondingly, the second side can then be the complementary rear side or front side. The main optical axis is perpendicular to a plane of the eye lens, in particular of the optical part, located axially between the first and the second side, in particular the front side and the rear side, such that the sides are disposed opposite to this plane viewed along the main axis.

Moreover, the eye lens includes a plurality of annular optical zones formed on at least one side, at least partly encircling the main optical axis, wherein zones each have at least one main sub-zone. An essential idea of the invention is to be regarded in that according to the first aspect the eye lens has a helix winding as an optical surface structure in addition to the annular zones such that this helix winding too contributes to the optical imaging characteristic of the eye lens. By the helix winding, a refractive power of the eye lens is varying in terms of value in encircling direction around the axis, wherein the helix winding is formed on at least one side of the optical part. By such a configuration of a multifocal eye lens, the depth of focus is improved such that the depth of focus is also substantially improved in at least two foci and thus two specific refractive powers of the eye lens besides sharp vision. Thereby, a corresponding improvement with respect to the known lenses from the prior art also occurs in this respect.

Thus, in the first aspect of the invention, multifocal eye lenses are encompassed, in which the annular optical zones are formed at least partly encircling and thus do not present completely closed rings. However, they can also be completely closed annular zones.

In particular, a refractive power portion is contributing to the overall refractive power of the lens by the helix winding, which varies in continuously increasing manner in terms of value in encircling direction around the optical axis and thus in azimuthal manner and thus in particular increases in terms of value from a winding start to a winding end of the helix winding, in particular continuously increases. In particular, this refractive power variation, as it is contributed by the helix winding, is formed without intermediate minimum in a complete turn around the optical axis.

Preferably, it is provided that the annular zones and the helix winding are formed and superimposed on a common side. This can be the front side or else the rear side. By such a configuration, the position of the two different separate surface structures or surface profiles can be very exactly achieved.

It can also be provided that the annular zones are formed on one side and the helix winding is formed on the other side. Therein, it can be provided that the annular zones are formed on the front side and the helix winding is formed on the rear side or the helix winding is formed on the front side and the at least partly encircling annular zones are formed on the rear side. In such a configuration, the individual separate surface structures or surface profiles can be very exactly produced in their contour such that the individual structures then allow very precise imaging characteristics.

It can also be provided that annular zones are formed at least partly encircling both on the one side and on the opposite other side. Similarly, it can be provided in addition thereto or instead of it that the helix winding is formed on the one side and also on the opposite other side. These two helix windings are then formed such that they in total constitute the entire azimuthal refractive power of the helix winding as a contribution to the overall refractive power of the eye lens. Compared to application of the helix winding only to one of the sides, in such a division, the optical effect with respect to the refractive power distribution is thus divided to the sides.

Preferably, it can be provided that at least some zones have a main sub-zone and a phase sub-zone. In such a configuration, a stepless topography, as already known from the prior art, with respect to the optical view and thus the wave front course is then again formed. With respect to the importance and technical configuration of a phase sub-zone, reference may be made to the facts already set out above.

In such a configuration, the formulas already mentioned above for an averaged refractive power and in particular the addition refractive power then preferably also apply.

However, in contrast thereto, here, the overall refractive power of the eye lens is then also azimuthally varying and can be described by the following formula:

$$F_{AV}(i,\alpha) = (1-p(i,\alpha))F_G(i,\alpha) + p(i,\alpha)F_S(i,\alpha) \quad (3)$$

Therein, (i) denotes the zone index and ($\alpha$) denotes the azimuthal angle. The formula is valid both for bifocal eye lenses and applicable to and modifiable for at least trifocal eye lenses, respectively. In the suggested general representation, thus, the averaged refractive power of the eye lens and in particular thus also the overall refractive power of the eye lens varies depending on the azimuthal angle ($\alpha$) and in particular also on the number of the zone as they are arranged in radial direction. In this context, a variation of the refractive power of the main sub-zone as well as a variation of the refractive power of the phase sub-zone as well as a variation of the area portion of the main sub-zone of this azimuthal angle and the zone index is indicated in the mentioned formula 3. In this context, a variation of all of these mentioned parameters of this azimuthal angle and the ring index or zone index can be provided, otherwise, implementations can also be provided, in which for example the main sub-zone is subjected to a corresponding variation and the other parameters do not include such a variation. Correspondingly, this can also be provided for a variation of the phase sub-zone without variation of the other parameters.

In particular, the azimuth-dependent overall refractive power of the eye lens composes according to the formula below:

$$F_{ges}(\alpha,\rho) = F_{Sph\ddot{a}re}(\alpha) + F_{Cylinder}(\alpha,\rho) + F_{HOA}(\alpha,\rho) + F_{EDoF}(\alpha,\rho) \quad (4)$$

with $\alpha$=azimuthal angle $\rho$=radial position on the optical part $F_{ges}$=azimuth-dependent overall refractive power $F_{Sph\ddot{a}re}$=spherical refractive power $F_{Cylinder}$=azimuth-dependent cylindrical refractive power portion $F_{HOA}$=azimuth-dependent refractive power portion for correcting higher-order aberrations (for example, coma, five-foil defect et cetera)

$F_{EDoF}$=azimuth-dependent refractive power portion for influencing the depth of focus Preferably, an area portion (p) of a main sub-zone of the overall area of a zone is $\geq 80\%$.

In particular, there applies: $F_{ges}(\alpha, \rho) = F_{AV}(i, \alpha)$

Implementations are also encompassed by the invention, in which a zone, in particular all of the zones, only has main sub-zones respectively, but does not have phase sub-zones. Such a configuration thus also allows the realization of a kinoform eye lens, which then also specifically has steps and thus is different from configurations of the eye lens with phase sub-zones.

The multifocal lens is formed as a diffraction lens. With respect to a ring density rm ($\alpha$), which thus also represents a normalization radius and describes a number of at least partly encircling annular zones per preset radius interval and thus virtually declares a lattice constant of the zones, it also contributes to a further description of the multifocal lens. The same then also applies to a phase deviation $\phi$, which virtually describes the optically effective offset between two adjacent zones in radial direction. Thus, the phase deviation also determines the energy division between the diffraction orders. The ring density determines the value of the diffractive addition refractive power, which means that it determines the angular distance of the diffraction orders.

In particular in combination with the above mentioned formula for the overall refractive power, which depends on the azimuthal angle, on the radial position on the respective optical side and the zone index with respect to its distribution, in particular in combination with the above mentioned local azimuth-dependent ring density, the phase deviation, optionally periodically alternating parameters, which are in particular required for trifocal and even higher focal configurations, a complete general description of the refractive power distribution of the eye lens can be effected. This too can be determined by means of known methods such as for example ray tracing, the wave front and/or the topography of a configuration of an optical part of the eye lens.

Preferably, it is provided that a main sub-zone refractive power contributing to the overall refractive power of the eye lens by the main sub-zone varies at least once in azimuthal direction around the main axis. In addition thereto or instead of it, it is advantageous if a phase sub-zone refractive power contributing to the overall refractive power of the eye lens by the phase sub-zone varies at least once in azimuthal direction around the main axis. Thereby, the refractive power distribution of such specific lenses with a main sub-zone and a phase sub-zone can be very individually and precisely influenced such that with multiple main refractive powers of the eye lens and thus with multiple foci of the eye lens, the depth of focus thereof can also be individually extended.

Preferably, it is provided that a phase deviation $\phi$ between two adjacent zones is in the interval $<\lambda$. Here, $\lambda$ relates to the configuration wavelength, which is preferably in the above already mentioned interval range.

By such small phase deviations, configurations are realized, which substantially also differ from stepped lenses with Fresnel zones since the phase deviation is usually a multiple of the configuration wavelength in such Fresnel lenses. Especially in configurations of the multifocal eye lens according to the invention, in which the zones and the zone transitions are stepless in terms of the above mentioned definition, a completely different configuration arises with respect to Fresnel lenses.

Preferably, it is provided that the phase deviation is constant in azimuthal direction around the main axis at least in one zone, in particular in the inner zones following outwards radially measured from the main optical axis. The main refractive powers—thus the refractive powers, which are increased considerably and in particular many times over other peaks in the intensity distribution of the refractive power spectrum—and thus the foci here practically do not experience any length extension in their intensity distributions.

In an advantageous implementation, it is provided that the phase deviation is varied in azimuthal direction around the main axis at least in one zone, in particular in the first zones counted radially outwards from the main optical axis. By a variation of the phase deviation in azimuthal direction, width and thus length extensions of individual main refractive powers and thus of individual foci in the intensity distributions can be achieved. Thereby, the individual foci of the eye lens can be very precisely and individually weighted with respect to their intensity distribution.

It can be provided that the phase deviation is steplessly varied.

Similarly, the variation of the phase deviation is also possible to the effect that a discrete phase deviation step is formed at least once in the complete turn around the main optical axis.

That adjustment is achieved by a phase deviation, how much light is divided between the zeroth and first diffraction order.

In an advantageous implementation, it is provided that the phase deviation is $=0$ over at least a first partial azimuthal interval and $\neq 0$ over at least a second partial azimuthal interval. In such an at least one-time discrete or continuous phase deviation variation in a turn around the optical axis, it is then in particular provided that a ratio between a far refractive power and a near refractive power of the eye lens is variable depending on the ratio between the first and the second partial azimuthal interval. This means that a quotient is generated depending on over which angular intervals the two partial azimuthal intervals respectively extend, wherein the division between the intensities of a far refractive power and a near refractive power, which represent main refractive powers of the eye lens, is then formed depending thereon.

It can also be provided that the phase deviation varies in radial direction such that a first phase deviation is for example formed between two radially consecutive zones, and a second phase deviation different thereto is formed between two further radially consecutive zones. This can be provided in implementations, in which the phase deviation between two zones varies in azimuthal manner, as well as in implementations, in which such an azimuthal variation is not formed.

In particular, it is provided that the helix winding is formed once encircling the main axis and a stepped transition is formed between a winding start and a winding end. By such a transition as discrete as possible, which is formed in azimuthal direction around the main optical axis over an angular range as small as possible, in particular $<20°$, in particular $<10°$, the varying, in particular continuously varying refractive power distribution in particular continuously increasing from the winding start to the winding end is favored in azimuthal direction. By a transition azimuthally as small as possible, the optical imaging characteristic of the eye lens is improved.

Preferably, it is provided that the eye lens has a toric refractive surface profile in addition to the annular zones and the helix winding, and this toric refractive surface shape is formed on at least one side of the optical part. By supplementing a toric refractive surface profile or surface shape, an astigmatism correction can also be effected. Here too, the toric refractive surface shape can be formed distributed on one or two sides.

In particular, it is provided that the transition is offset in azimuthal direction with respect to a flat main meridian of the toric refractive surface shape. In particular, the stepped transition is offset in azimuthal position around the main optical axis in an azimuthal angle between 20° and 70°, in particular between 40° and 50°. It can also be provided that the stepped transition is formed in azimuthal position around the main optical axis in an azimuthal angle between 220° and 250°, in particular between 220° and 230°, to a flat main meridian of the toric refractive surface. Preferably, the azimuthal position shift between the stepped transition and the flat main meridian is between $(\frac{1}{4}\pi)+/-(\frac{1}{8}\pi)$ or $(\frac{5}{4}\pi)+/-(\frac{1}{8}\pi)$. In these specific positions, the thickness of the lens can be considerably reduced in the direction of the main optical axis and thus be minimized in this respect. Thereby, the small incision capability is increased, which means that the lens can be very small folded and be introduced into the eye as an intraocular lens through an incision in the eye as small as possible.

In particular, this azimuthal angular offset relates to an azimuthal center of the transition forming azimuthally over a finite width, in particular a center in a projection of the transition into a plane perpendicular to the main optical axis.

Preferably, it is provided that the eye lens is at least bifocally formed and thus has at least two main refractive powers, which are a far refractive power and a near refractive power. Thus, the eye lens has n≥2 foci and the helix winding is formed in an implementation such that maximally n−1 foci are increased in depth of focus by the helix winding. Thereby too, an individual configuration of an eye lens with respect to its characterization of the imaging characteristics in the individual foci is achieved.

A further aspect of the invention relates to a multifocal lens with an optical part, which characterizes the optical imaging characteristics of the eye lens. The optical part has a first optical side and an opposite second optical side viewed in the direction of a main optical axis of the eye lens. The optical part moreover includes a plurality of annular optical zones formed on at least one side, at least partly encircling the main optical axis. Zones each have at least one main sub-zone, wherein a phase deviation is formed between two adjacent zones. An essential idea of the second aspect of the invention is to be regarded in that this phase deviation between at least two adjacent zones consecutive and adjoining in radial direction varies at least once in azimuthal direction and thus in encircling direction around the main optical axis. By such a configuration, the imaging characteristics of multifocal eye lenses can be improved and variability and flexibility with respect to the configuration of the individual main refractive powers and thus of the foci of this eye lens are achieved. Because of an azimuthally varying phase deviation, individual main refractive powers and thus foci of the eye lens can be individually influenced and configured in particular also independently of other foci, and in particular the intensity distribution of at least a specific focus can be specifically configured in this context. For example, expansion of the intensity distribution can here be effected such that the depth of focus can then also be individually and specifically increased in this specific focus.

Advantageous configurations of the variation of the phase deviation in azimuthal and/or radial manner are already mentioned in the first aspect of the invention with the respectively occurring advantages and also apply to the second aspect of the invention to full extent.

Moreover, configurations of the first aspect of the invention are also to be regarded as advantageous implementations of the second aspect of the multifocal eye lens.

A further advantageous configuration is to be regarded in that a radius of at least one zone is varied at least once in azimuthal direction around the main optical axis. Thereby, zones can also be formed, which do not have strictly a radius and thus a circular arc path over their entire azimuthal length, but which can also for example be formed as polygon-like partial rings or then also complete polygon rings.

Preferably, it is provided that radii of multiple zones are azimuthally varying at least once and the azimuthal position of the variation is identical in the multiple zones. Thereby, multiple zones consecutive in radial direction are virtually provided, which are formed identical in the shape with regard to their azimuthal contour configuration.

Thereby too, individual configurations of individual main refractive powers and thus foci of the multifocal eye lens can be achieved.

Preferably, it is provided that a first surface sector in the shape of a spherical surface wedge and at least a second surface sector in the shape of a spherical surface wedge are formed on a side of the optical part in azimuthal direction around the main axis, which are formed without overlap in azimuthal direction. Preferably, it is provided that the zone number and/or the area sizes of the zones are different in the at least two surface sectors. Thereby too, a topography of at least one side of the optical part can be very individually configured and thus optical imaging characteristics of the multifocal lens can be specifically influenced such that in particular the depth of focus in at least one focus of the eye lens can be individually influenced here too.

Advantageous implementations of the second aspect of the invention can also be advantageous implementations of the first aspect of the invention.

A further third aspect of the invention relates to a multifocal eye lens with an optical part, by which the optical imaging characteristics of the eye lens are characterized. The optical part has a first optical side and an opposite second optical side viewed in the direction of a main optical axis of the eye lens. The optical part includes a plurality of annular optical zones at least partly encircling the main optical axis at least on one side, wherein zones each have at least one main sub-zone and a phase deviation is formed between two adjacent zones. The zones are formed adjacent in radial direction and disposed adjoining to each other.

An essential idea of the third aspect of the invention is to be regarded in that an overall refractive power of the eye lens varies in increasing manner in azimuthal direction in a turn around the main axis without intermediate minimum. This means that it increases in a single turn around the optical main axis starting from a first value of the overall refractive power at a beginning to a second value of the overall refractive power at an end of this complete turn and a minimum does not occur therebetween. Such a configuration without intermediate minimum also allows a very individual increase of a depth of focus of the multifocal lens in at least one specific focus and thus in at least one specific main refractive power. In particular in multifocal eye lenses, in which the mentioned annular zones at least partly encircling the main optical axis have a main sub-zone and a phase sub-zone, the second and third aspects of the invention are also advantageous.

Implementations of the first aspect of the invention and/or implementations of the second aspect of the invention are to be regarded as advantageous implementations of the third aspect of the invention.

Especially in configurations of an eye lens as an intraocular lens, it is then disposed in the eye with an immersion medium, the aqueous humor, with its refractive index $n_{med}$ of 1.336.

In the configuration of a multifocal eye lens, in which zones are constructed of a main sub-zone and a phase sub-zone, the main sub-zones are also annular formations at least partly encircling the main optical axis. Similarly, the phase sub-zones are then annular formations at least partly encircling the main optical axis. A main sub-zone directly adjoins to a phase-sub-zone of a considered zone in radial direction. Collectively, the at least one main sub-zone and the at least one phase sub-zone of such a zone constitute the entire radial extension of the considered zone.

The specific values of parameters and indications to ratios of parameters or parameter values specified in the documents for defining embodiments of the eye lens are to be considered as encompassed by the scope of the invention even within the scope of deviations, for example due to measurement errors, system errors, DIN tolerances et cetera, whereby explanations relating to substantially corresponding values and indications are also to be understood thereby.

BRIEF DESCRIPTION OF THE DRAWINGS

The invention will now be described with reference to the drawings wherein:

FIGS. 2A to 2H are a representation of an embodiment of an eye lens according to the invention with specific parameter values and diagrams, in which parameters are represented depending on the azimuth, as well as a schematic three-dimensional surface representation of a side of an optical part of the eye lens;

FIGS. 3A to 3G are a representation of a second embodiment of an eye lens according to the invention with specific parameter values and diagrams, in which parameters are represented depending on the azimuth and the radius, respectively, and a schematic representation of a three-dimensional surface of a side of an optical part of the eye lens of this embodiment;

FIGS. 4A to 4E are a representation of a further embodiment of an eye lens according to the invention with specific parameter values and individual parameters depending on the azimuth as well as a schematic representation of a three-dimensional surface of a side of an optical part of the eye lens;

FIGS. 5A to 5G are a further embodiment of an eye lens according to the invention in specific parameter values as well as diagrams, in which parameter values are represented depending on the azimuth and the radius, respectively, and a schematic representation of a surface profile of a side of an optical part of the eye lens;

FIGS. 6A to 6G are a representation of a further embodiment with specific parameter values and diagrams, in which parameter values are represented depending on the azimuth and on the radius, respectively, as well as a schematic representation of a three-dimensional surface shape of a side of an optical part of the eye lens;

FIGS. 7A to 7I are a representation of a further embodiment of an eye lens according to the invention with specific parameter values and diagrams, in which parameters are represented depending on the azimuth and the radius, as well as a schematic representation of a three-dimensional surface shape of a side of an optical part of the eye lens;

FIGS. 8A to 8G are a further embodiment of an eye lens according to the invention with specific parameter values and diagrams, in which parameters are represented depending on the azimuth and the radius, as well as a schematic representation of a three-dimensional surface shape of a side of an optical part of the eye lens;

FIGS. 9A to 9H are a representation of a further embodiment of an eye lens according to the invention with specific parameter values and diagrams, in which parameters are represented depending on the azimuth and the radius, respectively, as well as a schematic representation of a three-dimensional surface shape of a side of an optical part of the eye lens;

FIGS. 10A to 10G are a further embodiment of an eye lens according to the invention with specific parameter values and diagrams, in which parameters are represented depending on the azimuth and the radius, respectively, and a schematic representation of a three-dimensional surface shape of a side of an optical part of this eye lens;

FIGS. 11A to 11H are a representation of a further embodiment of an eye lens according to the invention with specific parameter values and diagrams, in which parameters are represented depending on the azimuth and the radius, respectively, and a schematic representation of a three-dimensional surface shape of a side of an optical part of the eye lens;

FIGS. 12A to 12G are a representation of a further embodiment of an eye lens according to the invention with specific parameter values and diagrams, in which parameters are represented depending on the azimuth and the radius, respectively, and a schematic representation of a three-dimensional surface shape of a side of an optical part of this eye lens;

FIGS. 13A to 13G are a representation of a further embodiment of an eye lens according to the invention with specific parameter values and diagrams, in which parameters are represented depending on the azimuth and the radius, respectively; and, FIGS. 14A to 14H are a further embodiment of an eye lens according to the invention with specific parameter values and diagrams, in which parameters are represented depending on the azimuth and the radius, respectively, as well as a schematic representation of a three-dimensional surface shape of an optical part of this eye lens.

DESCRIPTION OF THE PREFERRED EMBODIMENTS OF THE INVENTION

Figure 1A:
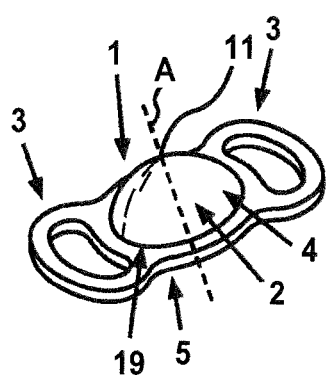
FIG. 1A is a perspective representation of a first embodiment of an eye lens according to the invention.

In the figures, identical or functionally identical elements are provided with the same reference characters.

In FIG. 1A, a first embodiment of an eye lens 1 is shown in a perspective representation, which is an intraocular lens. The eye lens 1 includes an optical part 2 and a haptic 3 subsequent thereto. The eye lens 1 is foldable and can be introduced into the eye via a small incision. The optical part 2, which is essential to the optical imaging characteristic of the eye lens 1, includes a main optical axis A. The optical part 2 moreover has a first optical face or side 4, which can be a front side, and opposite a second optical face or side 5, which can be a rear side, viewed in the direction of this main optical axis A. The exemplary front side 4 faces the cornea in the implanted state of the eye lens 1 in the eye, whereas the rear side faces away from this cornea.

Figure 1B:
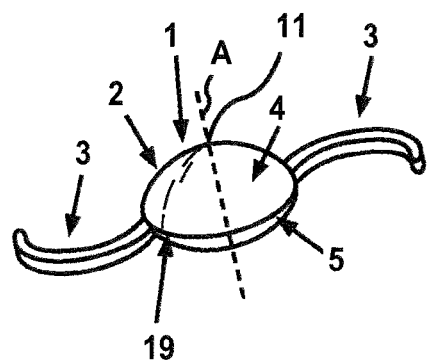
FIG. 1B is a perspective representation of a further embodiment of an eye lens according to the invention.

In FIG. 1B, a further embodiment of an eye lens 1 formed as an intraocular lens is shown in a perspective representation. It differs from the implementation in FIG. 1A by the different haptic 3. The eye lens 1 is retained in the eye by means of the haptic 3.

Basically, otherwise formed and configured haptics 3 can also be provided.

In FIG. 2A, a parameter set for an embodiment of a multifocal eye lens according to the invention is specified. Therein, $P_0$ denotes a basic refractive power of the eye lens in diopters, "add" denotes an addition refractive power, in particular a diffractive addition refractive power, $n_1$ denotes the refractive index of the aqueous humor, in which the eye lens formed as an intraocular lens is located, $n_2$ denotes the refractive index of the material of the intraocular lens, in particular of the material of the optical part. Moreover, ct denotes the center thickness of the eye lens along the axis A, which here is exemplarily 1 mm, λ denotes the underlying configuration wavelength, which here is exemplarily 546 nm, Δλ denotes a phase deviation between radially adjacent zones, (k) denotes the conic constant of the envelope asphere and "frac" denotes the area portion of a main sub-zone of the entire area of the considered zone, respectively, rm denotes the maximum radius of the optical part in millimeters, $s_{max}$ denotes the zone number of the optical zones on this standard radius.

Moreover, "cyl" or $F_{cyl}$ denotes the cylindrical refractive power and thus the refractive power portion of the overall refractive power $F_{Ges}$ of the eye lens, which is contributed by a toric refractive surface area or surface shape. "sph" or $F_{Sphäre}$ denotes the spherical refractive power, which proportionally contributes to the overall refractive power of the eye lens. Moreover "edof" or $F_{EDoF}$ denotes the refractive power portion contributed to the overall refractive power of the eye lens by a helix winding. Moreover HOA1 and HOA2 or $F_{HOA1}$ and $F_{HOA2}$ denote refractive power portions to the overall refractive power of the eye lens, which contribute to the correction of higher-order aberrations. The refractive powers are indicated in diopters.

In this first embodiment, thus, a multifocal eye lens is explained, which additionally has a helix winding besides annularly formed zones, of which the zones each have a main sub-zone and a phase sub-zone, which encircles the main optical axis A one time. Moreover, in the configuration according to FIGS. 2A to 2H, the phase deviation ϕ is constant.

In FIG. 2B, the overall refractive power $F_{Ges}$ of the eye lens 1 is represented depending on the azimuth of a turn in a diagram. As is apparent, the overall refractive power continuously increases and moreover is stepless.

In FIG. 2C, in contrast, a diagram is shown, in which the azimuthal refractive power $F_{EDof}$ is represented depending on the azimuth. By this refractive power portion, the depth of focus is specifically adjusted and increased. As it is apparent from the diagram according to FIG. 2C, a continuously increasing course is given here too, which is stepless, and a refractive power difference of 1 diopter is then generated in a stepped transition between a winding start and a winding end of the helix winding.

By the course of this azimuthal refractive power distribution shown in FIG. 2C, a different weighting in the single azimuthal angles is also achieved. The refractive powers present at the winding start and at the winding end are more intensely weighted since they are present over a larger angular range or a lower variation occurs than in an angular interval located therebetween.

Figure 2D:
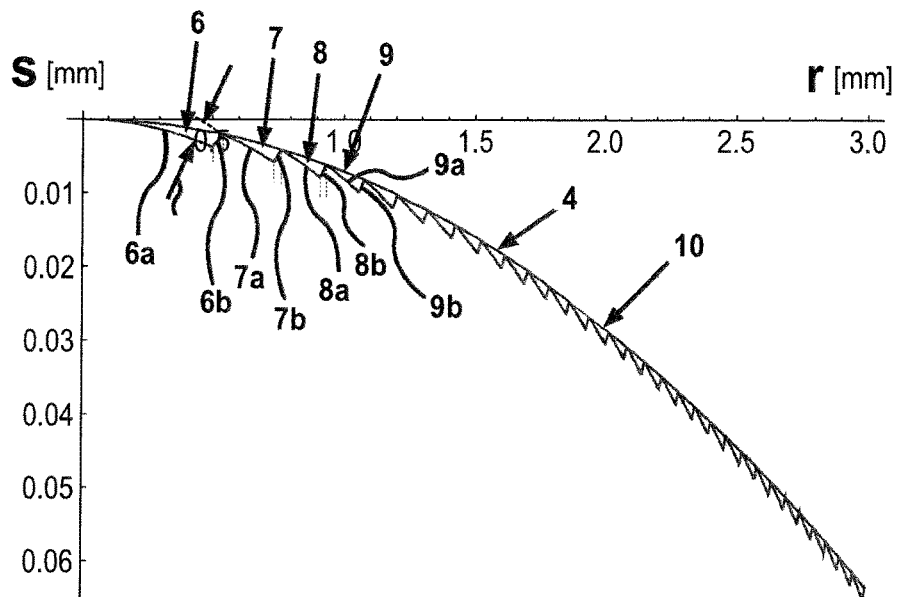

In FIG. 2D, a diagram is shown, in which the sagittal height S and thus the height in the direction of the optical axis A is shown depending on the radius of the optical part 2. Here, a sectional representation of the side 4 of the optical part 2 is shown, wherein only half of the entire sectioned contour is shown.

As is apparent, a plurality of annular zones at least partly encircling the axis A is formed in this embodiment, of which only the zones (6, 7, 8, 9) located inside viewed outwards from the axis A, which directly radially adjoin to each other, are provided with a reference character for the sake of clarity. The zone 6 has a main sub-zone 6a and a phase sub-zone 6b. A zone 7 then radially following also has a main sub-zone 7a and a phase sub-zone 7b. The same applies to the zones 8 and 9, which then also have main sub-zones 8a and 9a as well as phase sub-zones 8b and 9b.

By this configuration, a refractive-diffractive surface is provided.

An envelope 10 is also exemplarily illustrated, which connects the tips of the phase sub-zones 6b to 9b as well as optionally all of the further present phase sub-zones.

In the embodiment, it is provided that the area portion of the main sub-zones 6a to 9a in the zones 6 to 9 is 85% of the overall area of the respective zones 6 to 9.

Such an area portion can also be even larger, and a configuration can also be provided, in which the area portion of a phase sub-zone is equal to 0. Thereby, a kinoform lens is then realized.

In FIG. 2D, moreover, a phase deviation ϕ is also drawn, as it is measured between two radially adjacent zones 6 and 7 adjoining to each other. Correspondingly, a phase deviation is also determined between each two other zones adjoining to each other. Here, the phase deviation ϕ preferably is a value, which is less than the configuration wavelength λ, in particular is between 0.3λ and 0.6λ.

Preferably, it is also provided in the embodiment according to FIGS. 2A to 2H that a relative intensity distribution of a far focus and a near focus is 65% to 35%. The eye lens 1 formed as an intraocular lens is in particular also mirror-symmetrically configured and aspherized in aberration-neutral manner with respect to its enveloping topography and thus the envelope 10.

By the azimuthally varying overall refractive power illustrated in FIG. 2B, the depth of focus value can be increased, in particular be increased on at least one of the mentioned foci of the eye lens 1.

In particular, it is provided that in the representation in FIG. 2C, the azimuthal course of the refractive power $F_{EDof}$ contributing by the helix winding is exemplarily a cosine function of the frequency of 0.5. However, manifold other configurations are possible for the curve course of the refractive power $F_{EDof}$.

Figure 2E:
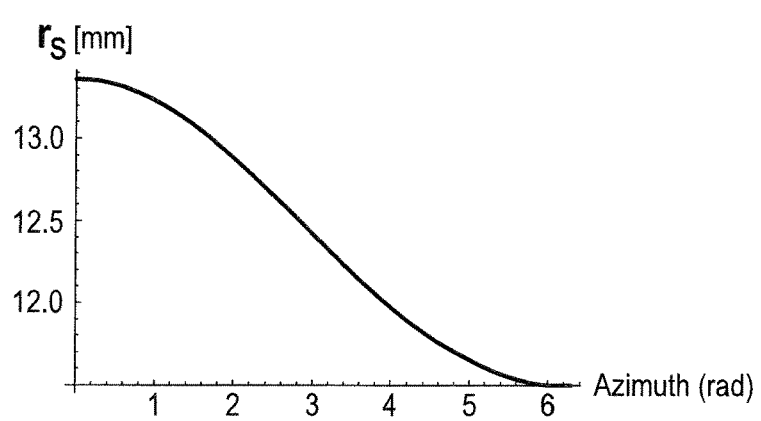

In FIG. 2E, a diagram is shown, in which the apex radius of curvature rs of the eye lens is represented depending on the azimuth. An apex 11 of the optical part 2 is exemplarily represented in FIG. 1A and FIG. 1B.

Figure 2F:
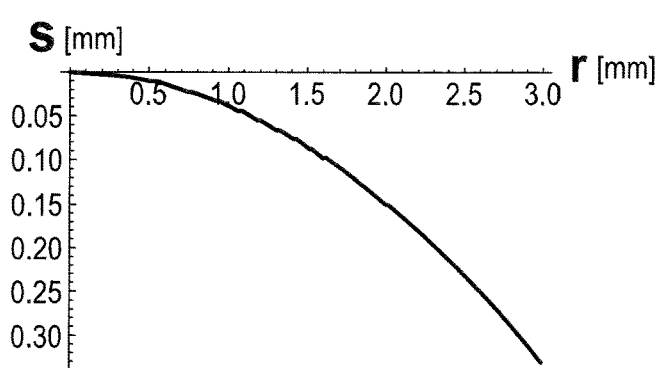

In the diagram according to FIG. 2F, the sagittal height S is shown depending on the radius (r) for the embodiment. At this place it is to be mentioned that the representation in FIG. 2D only is to represent the structuring of the surface and is to clarify the configuration of the zones 6 to 9 as well as the orientations of the main sub-zones 6a to 9a and the phase sub-zones 6b to 9b to that effect. The representation exact in terms of value for the embodiment is indicated in the diagram according to FIG. 2F.

Figure 2H:
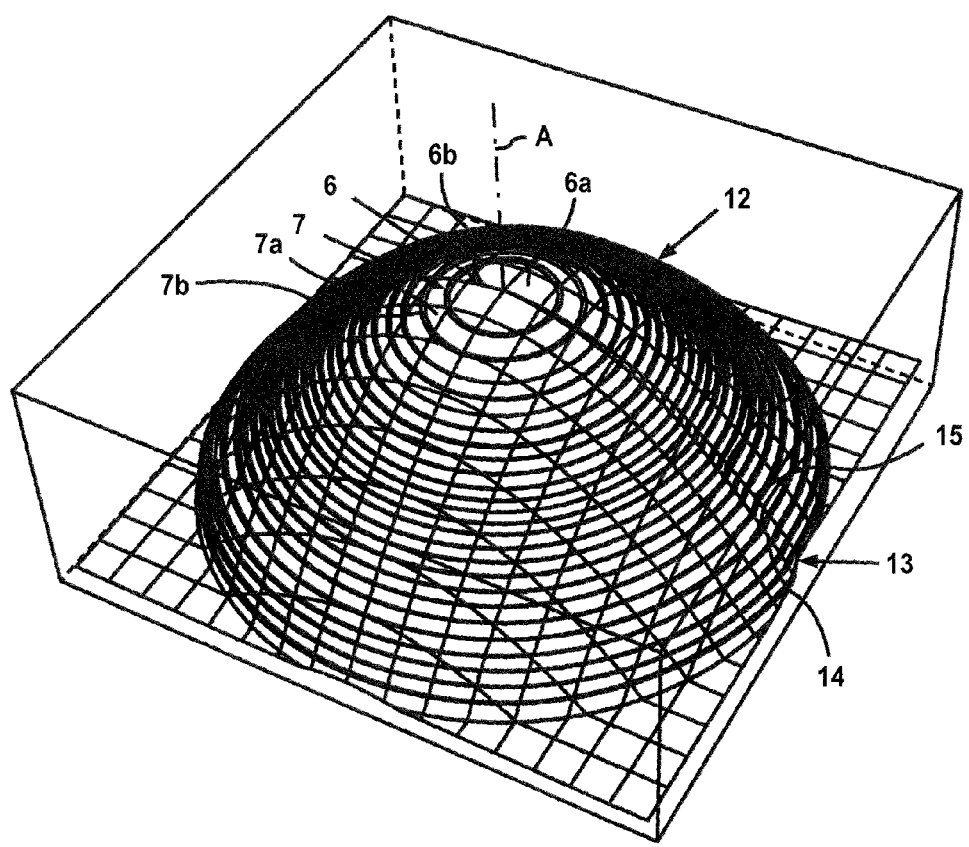

In FIG. 2H, a three-dimensional surface topography of the side 4 is shown in a schematic representation. Here, it is recognizable that the annular zones 6 to 9 are apparent.

Moreover, the helix winding 12 once encircling the main optical axis A is also apparent. This helix winding 12 has a winding start 14 and a winding end 15. A stepped transition 13 is configured between the winding start 14 and the winding end 15. It has an azimuthal angular range as low as possible such that it is formed as small as possible and minimized in this respect.

At the same time, the winding start 14 also represents a boundary edge of the transition 13, wherein the same also applies to the winding end 15. In the embodiment, the winding start 14 represents a radial course, which is flatter than the radial course of the winding end 15. The sagittal height S can be determined according to the formula below:

$$s(r, r_0, Q) = \frac{r^2}{r_0 \left(1 + \sqrt{1 - (1+Q)\frac{r^2}{r_0^2}}\right)} \quad (3)$$

r=radial position on lens surface
$r_0$=central radius of curvature ($r_0 \rightarrow r_{target}$=radius of curvature of the target function (enveloping surface))
Q or k=conic constant This equation for the sagittal height describes the radial course of a conic asphere. It can be generalized by addition of polynomial coefficients or be replaced with other types of description, for example by Zernike series, polynomials, splines or Bezier curves. By the variation of the asphericity, for example by variation of the conic constant Q or (k), the azimuth-dependent radial refractive power course can be influenced. Thereby, imaging errors by spherical aberration can also be compensated for. The calculation of the sagittal height S in each azimuth directly results in the enveloping three-dimensional topography of the lens surface and thus serves as a target function for calculating the refractive surface. This enveloping target function is illustrated by the envelope 10 in FIG. 2D.

By the helix winding 12, starting from the winding start 14 and a refractive power value linked thereto, a continuous increase of the refractive power value up to the winding end 15 is achieved, wherein this is characterized by the exemplary curve course in FIG. 2C.

As already mentioned, each of the concentric and rotationally symmetrical main zones 6a to 9a has a phase deviation φ of preferably 0.46λ to its main zone adjacent on both sides in radial direction. This then in particular results in the already mentioned intensity distribution of 65% to 35% between the far focus and the near focus.

In FIG. 2G, a diagram is shown, in which a focus shift and thus the length extension or the widening is illustrated, whereby the depth of focus can also be recognized as an increase of the far focus and the near focus compared to configurations without such a helix winding.

From FIG. 2G, it is apparent that with a diffractive addition refractive power of 3.75 diopters and a pupil size of 3 mm, which corresponds to the maximum radius of the optical part 2, a depth of focus range of substantially 1.8 diopters each occurs for the near focus and the far focus.

With respect to a lens from the prior art, this corresponds to a substantial gain of depth of focus of circa 85% with a pupil of 3 mm. This considerable gain of depth of focus reduces the sensibility of the optical imaging characteristics with respect to defocusing errors.

Figure 3C:
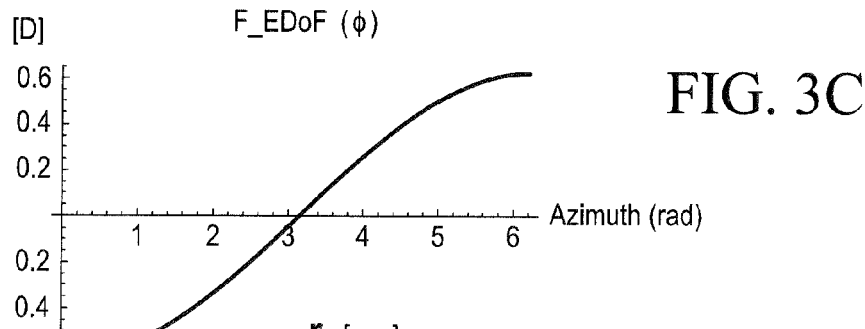
Figure 3D:
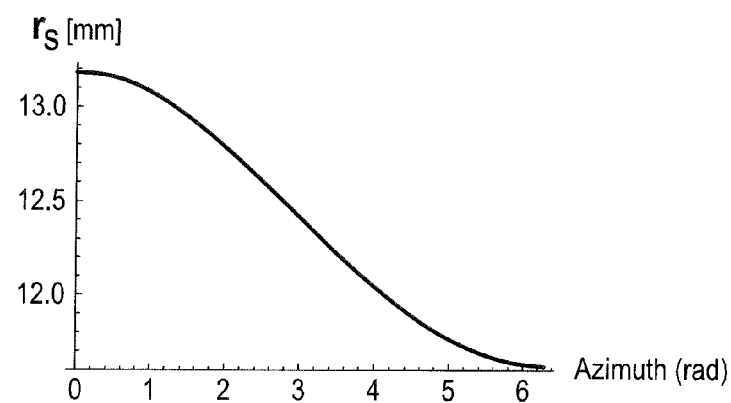
Figure 3E:
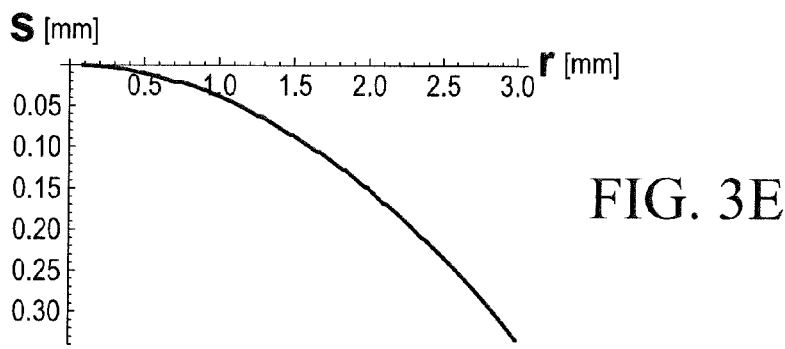

In FIG. 3A, a parameter value indication of a parameter set for a further embodiment of an eye lens according to the invention is again represented.

With respect to the diagrams in FIGS. 3B, 3C, 3D and 3E, specific parameters of the parameter set according to FIG. 3A are again represented depending on the azimuth.

Figure 3F:
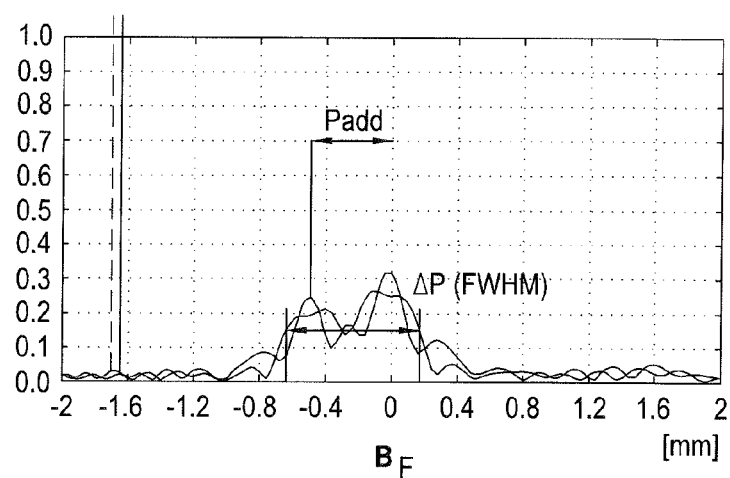

In FIG. 3F, the width $B_F$ is again characterized by the indication of the full width at half maximum such that the widening by the embodiment of the eye lens according to the invention is apparent compared to the also illustrated width value in the prior art.

In the embodiment according to FIGS. 3A to 3G, thus, an embodiment is shown, as it has a helix winding besides the annular zones analogously to the embodiments in FIGS. 2A to 2H and in which the phase deviation between two radially adjoining zones is constant in azimuthal direction. This in particular then also applies to all of the zones of the eye lens 1.

Figure 3G:
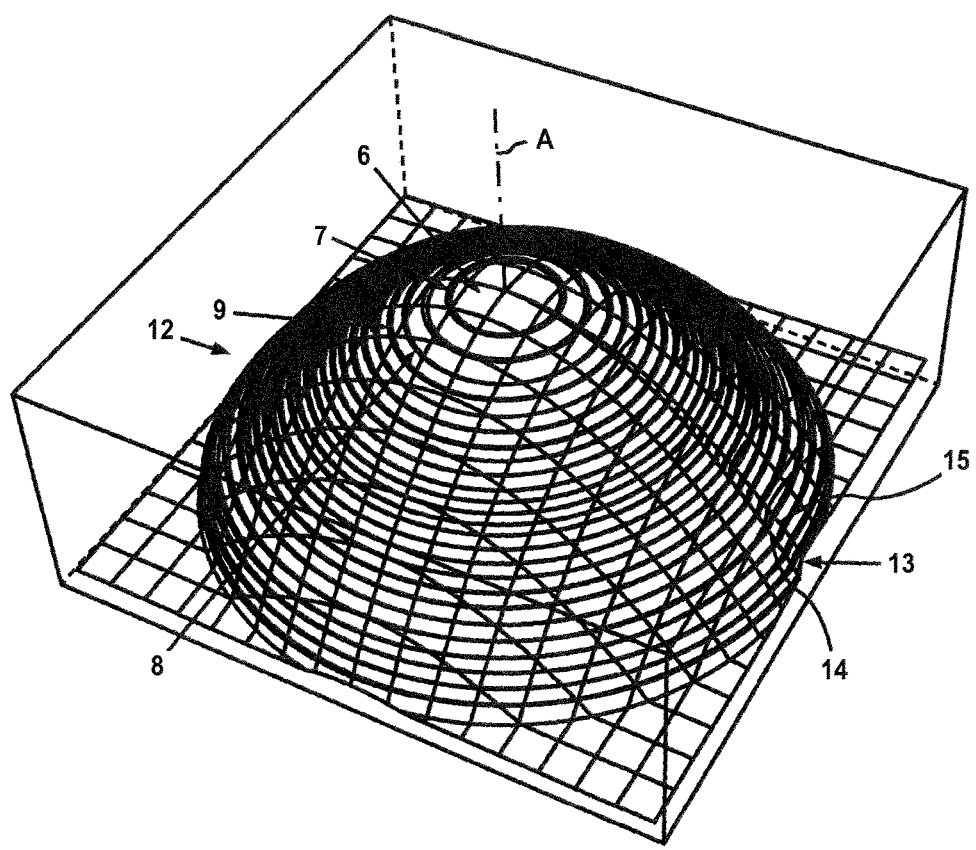

In FIG. 3G, a schematic three-dimensional surface topography of the side 4 of this example is shown.

In FIGS. 4A to 4E, a further embodiment with specific parameter values and courses of parameters depending on the azimuth and the radius is illustrated, respectively. In this embodiment, the eye lens includes annular zones and the phase deviation φ between two radially adjacent zones is constant in azimuthal direction. This is also correspondingly present in the previous embodiments. Moreover, in the embodiment according to FIGS. 4A to 4E, a toric refractive surface shape 16 is additionally present. In this embodiment according to FIGS. 4A to 4E, however, a helix winding is not formed. However, such one can also be provided and for example be superimposed with the toric refractive surface profile or the surface shape 16 and the annular zones 6 to 9 on one side, for example the side 4.

Figure 4D:
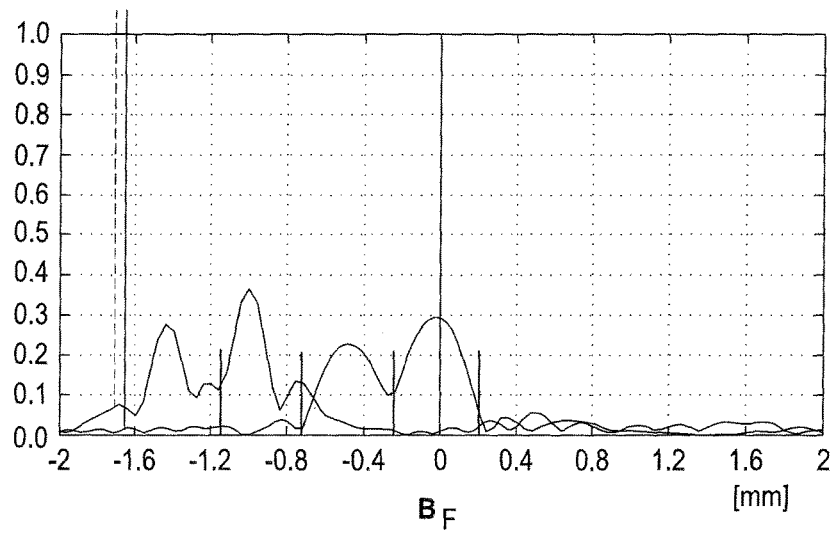
Figure 4E:
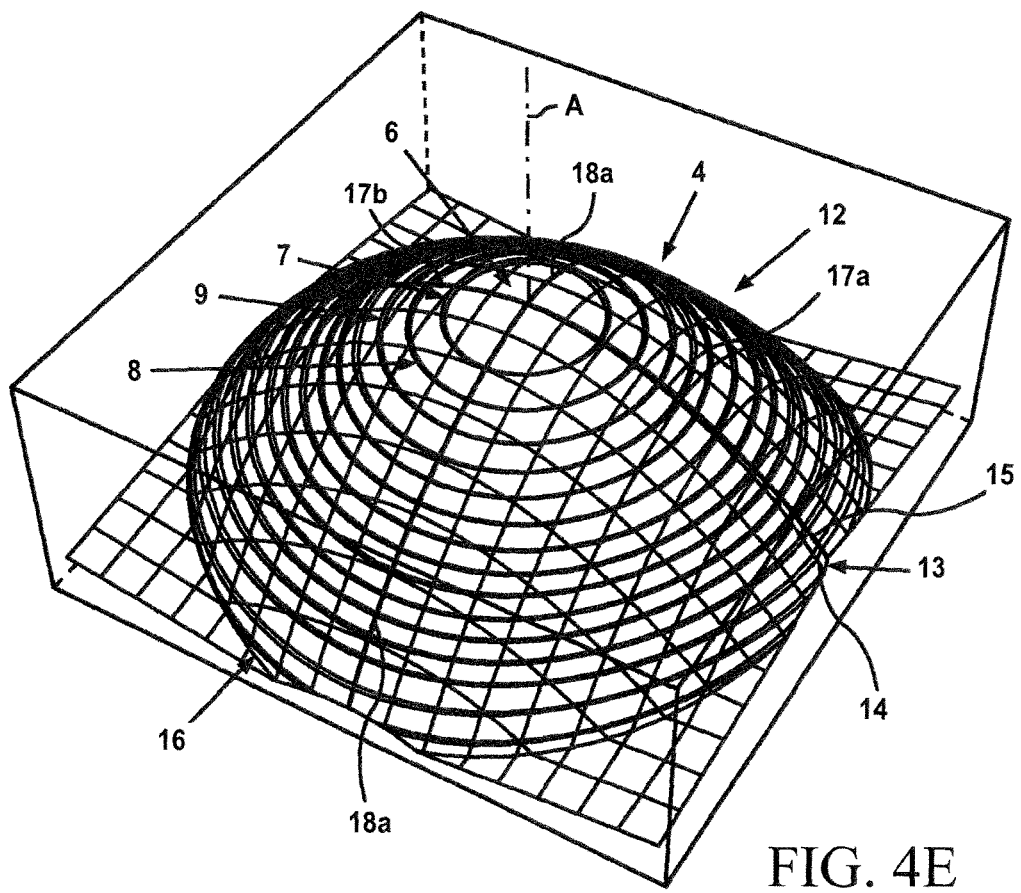

As exemplarily illustrated in FIG. 4E, this toric refractive surface shape 16 has perpendicular main meridians 17a, 17b and 18a, 18b. By the superposition of the helix winding 12, the main meridian sections 17a and 17b have different radii, in particular apex radii of curvature. The same applies to the main meridian sections 18a and 18b.

In the shown implementation, the main meridians 15a and 15b show the flatter sections, whereas the main meridians 16a and 16b represent the steeper ones.

In FIGS. 4A to 4E, a further embodiment of an eye lens 1, which is formed as an intraocular lens, is shown. In this implementation, it is provided that a helix winding 12 and a toric refractive surface profile or a toric refractive surface shape 16 are present besides the annular zones. Here, the main meridians are perpendicular to each other and the meridian sections 17a and 17b have the flatter radius with respect to the median sections 18a and 18b.

For the rest, by the diagrams according to FIGS. 4B, 4C, 4D, the apex radius $r_s$, the sagittal height S depending on the azimuth and the radius, respectively, are then again represented and the focus width $B_F$ is shown.

In FIGS. 5A to 5F, a further embodiment of an eye lens 1 according to the invention is explained. In this implementation, a toric refractive surface shape 16 is formed besides annular zones. In this embodiment, the phase deviation between two adjacent zones 6 to 9 is also respectively constant in azimuthal direction. In this embodiment, the eye lens does not have a helix winding. However, an implementation can here also be provided, which also additionally has a helix winding based on the underlying parameters and parameter values and/or a phase deviation φ varies in azimuthal direction.

Figure 5D:
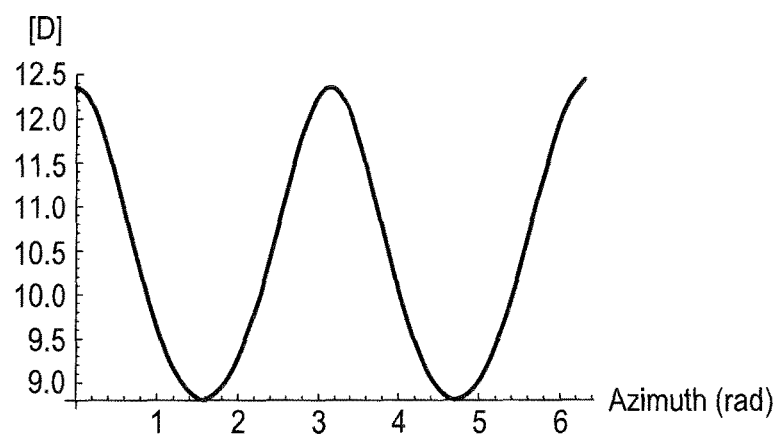
Figure 5E:
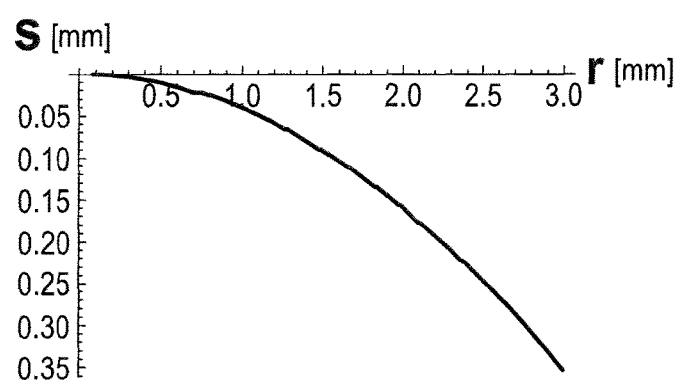
Figure 5F:
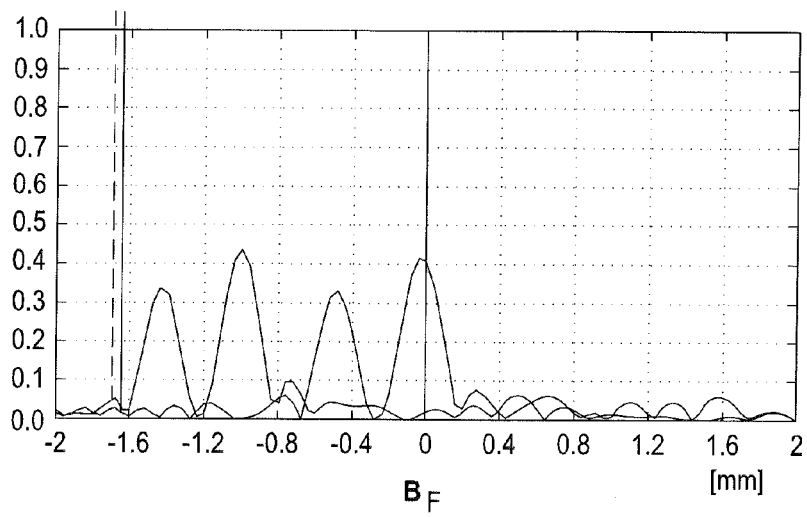
Figure 5G:
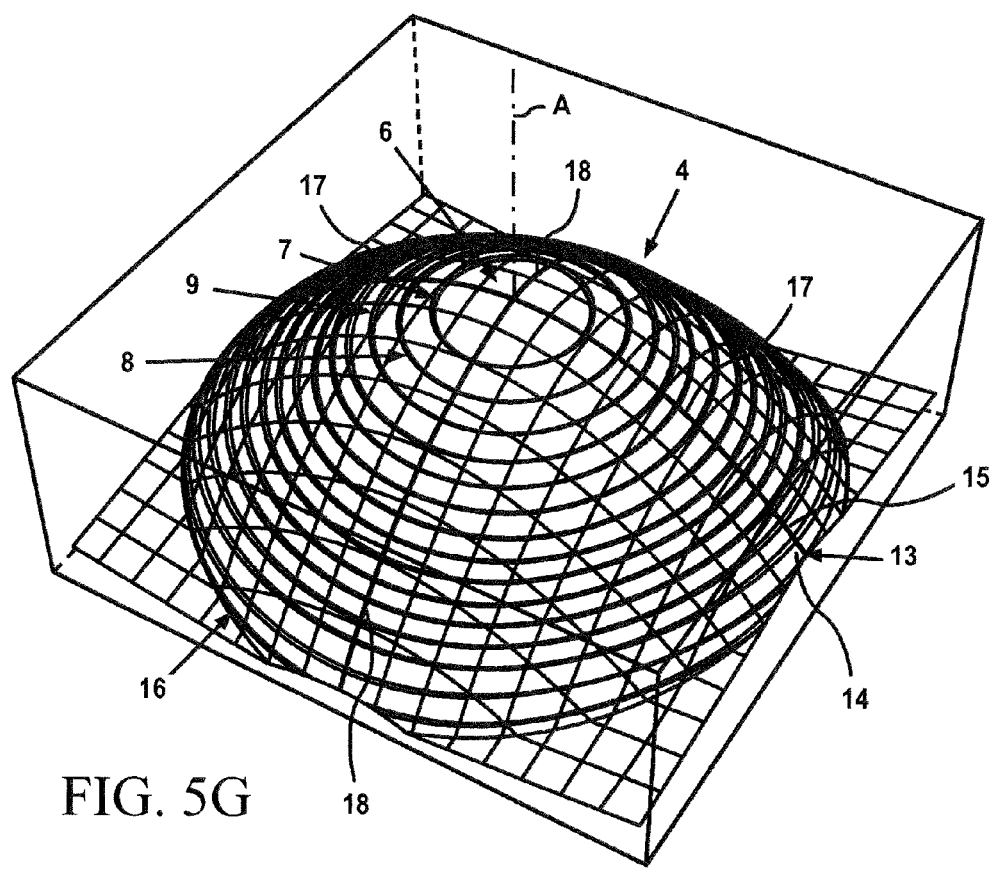

In FIG. 5G, a schematic three-dimensional representation of the surface geometry of a side 4 of the optical part 2 is again illustrated, wherein all of the profile portions are formed on this side here too.

In this configuration, the main meridians, the flat main meridian 17 and the steep main meridian 18 are each identically configured on the left and right side of the main optical axis A such that sections with different radii of curvature, in particular apex radii of curvature, as it is shown in FIG. 4E, are not present.

Figure 6E:
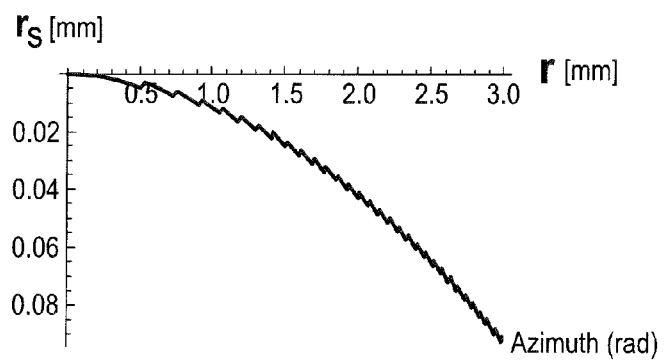

In FIGS. 6A to 6G, a further embodiment of an eye lens is shown. In this implementation, the eye lens 1 has a phase deviation φ, as it is shown in the course according to FIG. 6C. The basic parameter values according to the listing in FIG. 6A are then represented with some parameters in the graph according to the diagrams in FIGS. 6B, 6C, 6D, 6E and 6F.

In this configuration, the phase deviation exemplarily varies according to the curve course in FIG. 6C and thus continuously increases. Here, the start is a specific beginning in azimuthal direction.

In the embodiment in FIGS. 6A to 6G, only annular zones 6 to 9 are formed, however, otherwise a helix winding or a toric refractive surface shape is not additionally formed or superimposed. However, an implementation can also be provided, in which a helix winding and/or a toric refractive surface shape are also additionally present.

Figure 6F:
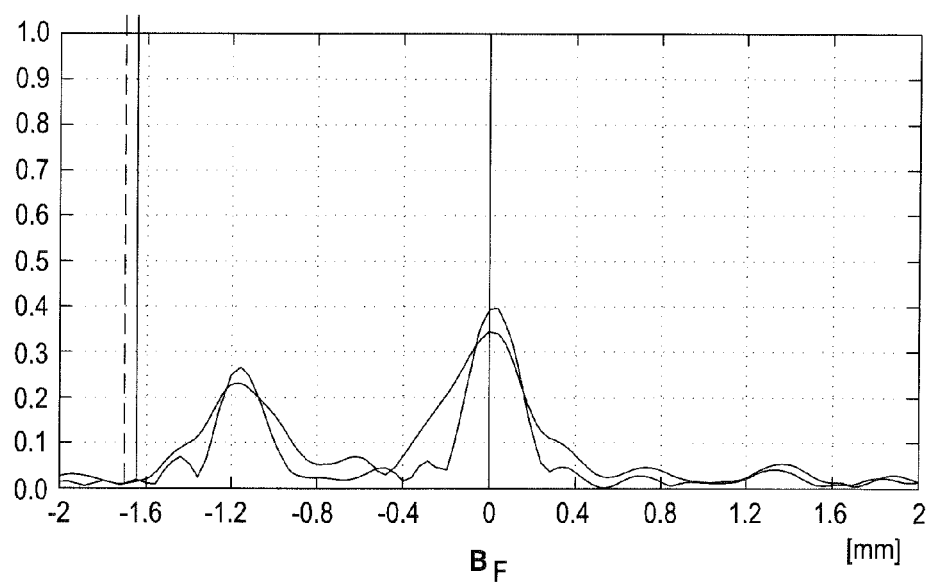

In FIG. 6F, the focus widening of the foci of the in particular bifocal lens is again shown.

Here too, it is to be mentioned that a trifocal, quadrafocal or beyond multifocal eye lens can also be formed in all of the implementations.

Figure 6G:
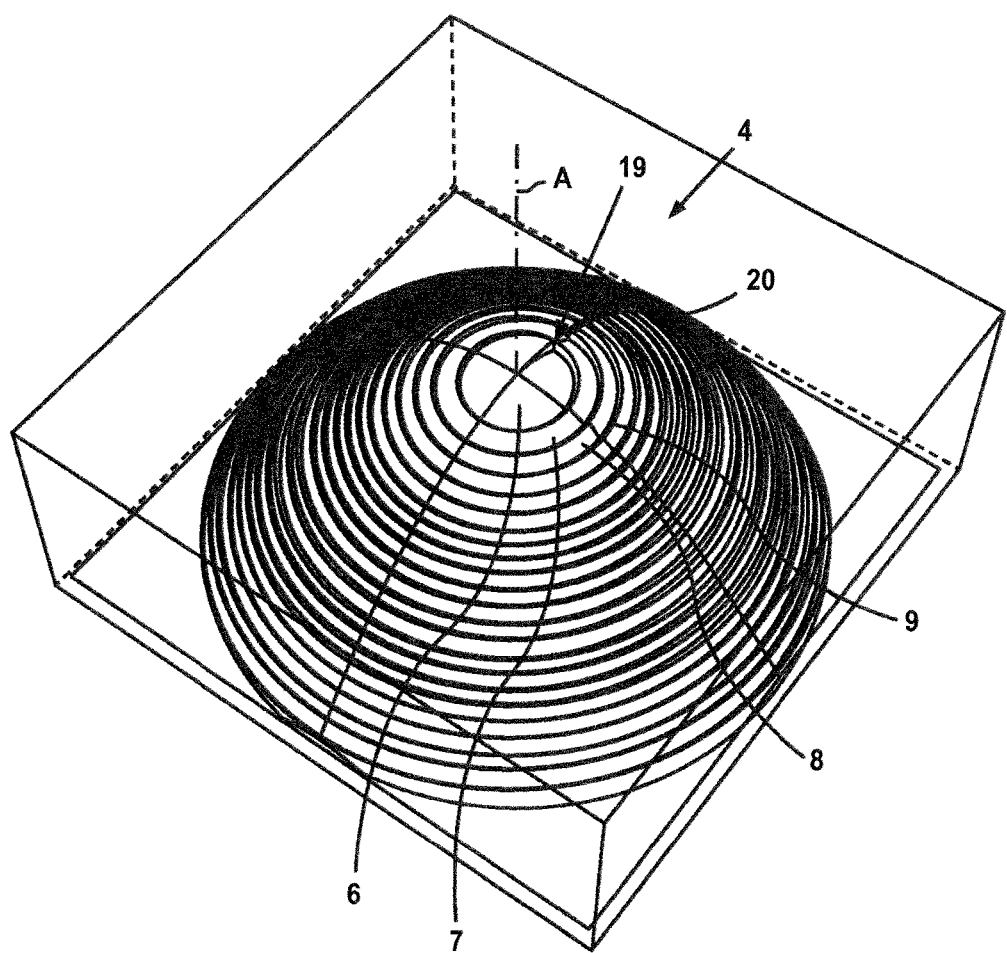

The course of the sagittal height S depending on the radius r is illustrated in the diagram according to FIG. 6E. Moreover, a schematic representation of a three-dimensional surface topography of the embodiment is shown in FIG. 6G. At an azimuthal start 19, between the zones 6 to 9, which are only exemplarily provided with a reference character for all of the further zones, the minimum phase deviation of 0 is formed, which then continuously increases extending around the axis A counter-clockwise in the embodiment, and then reaches the maximum at an end 20. This phase deviation course is identically formed both in a main sub-zone and in a phase sub-zone of the zones 6 to 9. This in particular applies to the first inner zones of the eye lens 1, in particular to all of the zones of the eye lens 1.

Figure 7D:
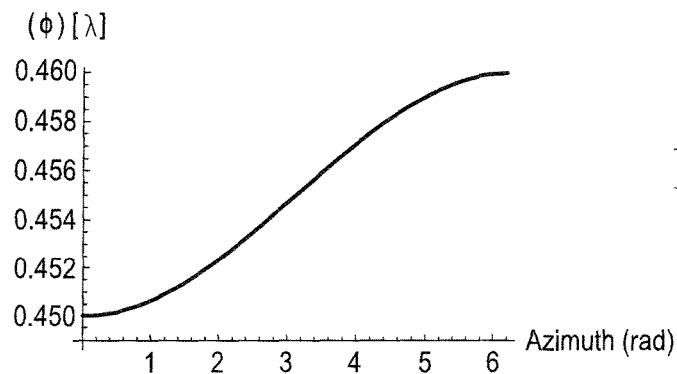
Figure 7E:
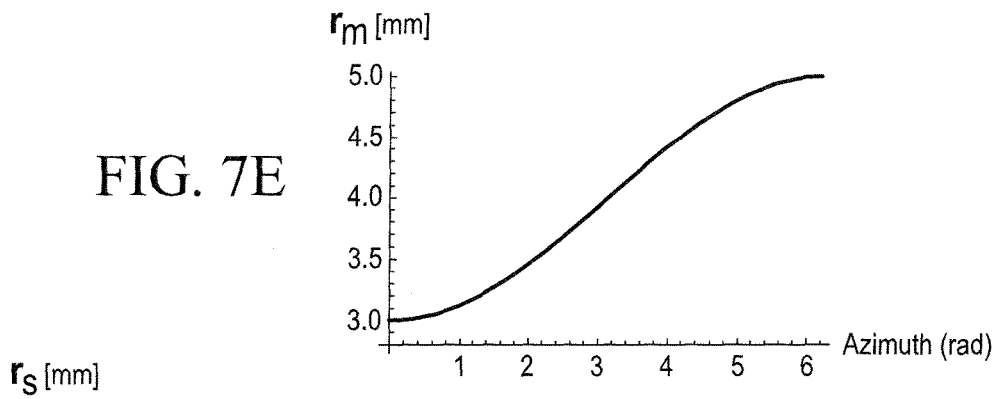
Figure 7F:
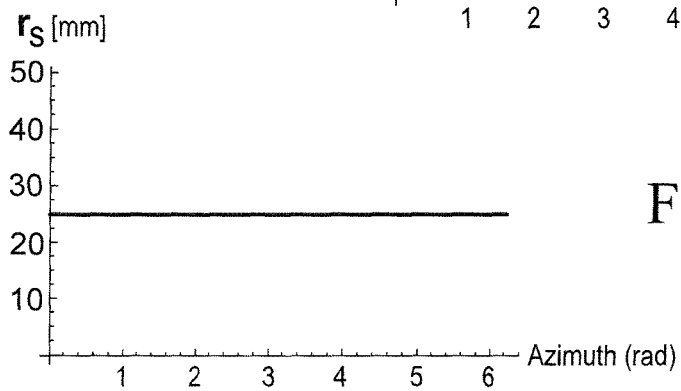
Figure 7G:
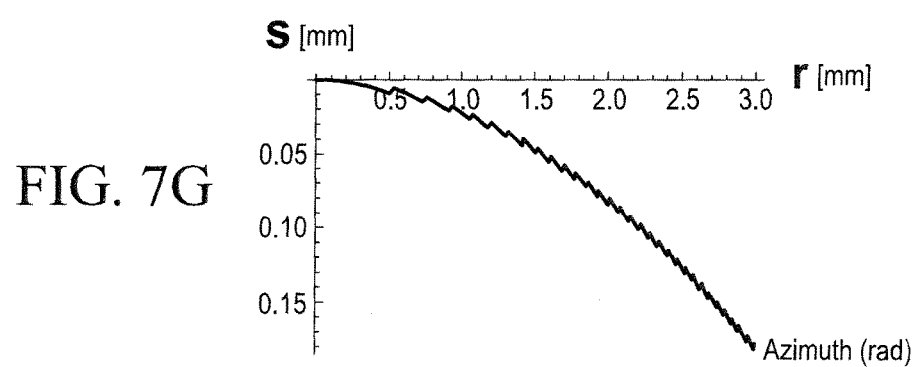
Figure 7H:
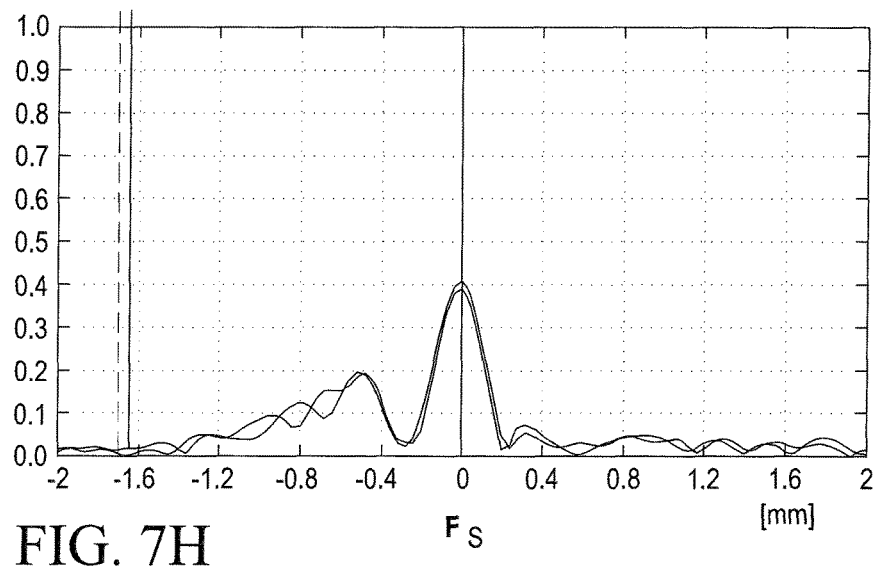
Figure 7I:
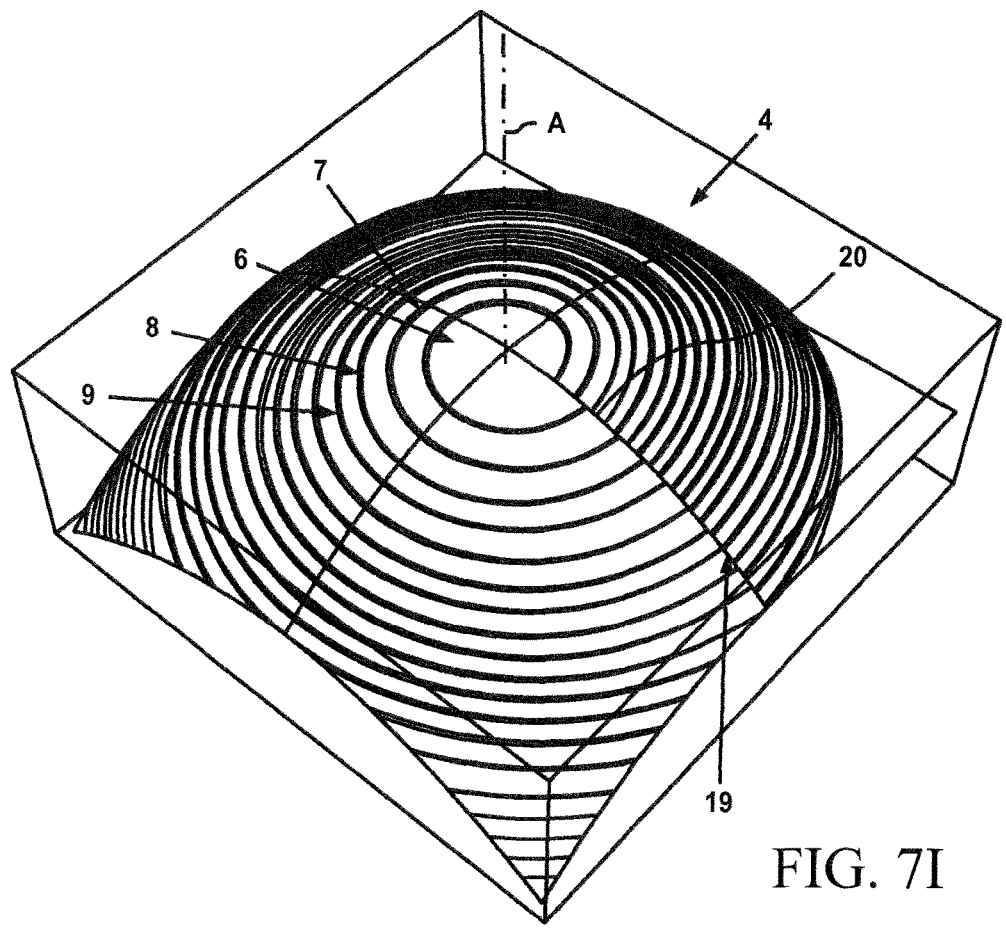

A further embodiment is shown in FIGS. 7A to 7I, wherein here the variation of the phase deviation ϕ is different unlike the configuration according to FIGS. 6A to 6G. Moreover, the parameter values of the basic refractive power $P_0$, the spherical refractive power $F_{Sphäre}$ and the standard radius rmmax and rmmin (both indicated in millimeters) are also varied with respect to the embodiment in FIGS. 6A to 6G. In FIGS. 6A and 7A, "phasemin" and "phasemax" denote the minimum phase deviation ϕ and the maximum phase deviation ϕ in a turn around the axis A.

Figure 8D:
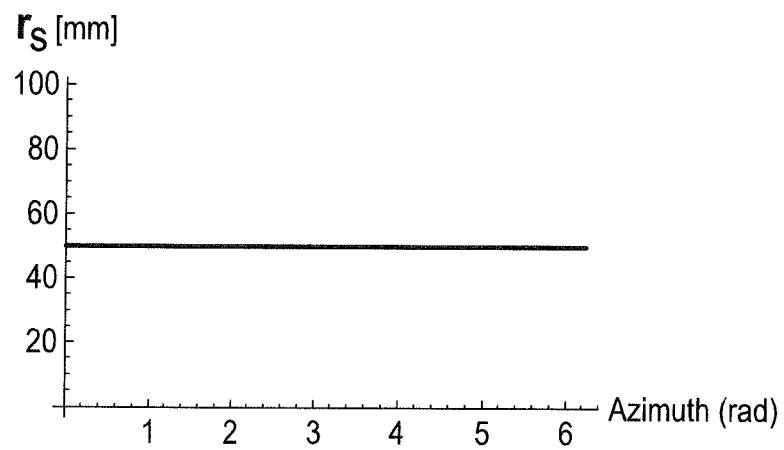

In the embodiment according to FIGS. 8A to 8F, an example is again shown, in which the phase deviation varies in azimuthal direction, however, a helix winding and a toric refractive surface shape are otherwise not formed. In this configuration, the phase deviation is discretely configured in a specific azimuthal interval, as it is illustrated in FIG. 8C. Both the azimuthal position and the height of the phase deviation are to be only exemplarily understood. The width of the azimuthal interval, over which this maximum phase deviation occurs, is also only exemplary. By such an embodiment, in which the exemplary three-dimensional surface topography is illustrated in FIG. 8G, the configuration of surface sectors in the shape of a spherical surface wedge of specific structuring can also be achieved. In this implementation, a surface sector 21 in the shape of a spherical surface wedge is realized, in which the zones 6, 7, 8 and 9 extend over an angular interval of about 120°. As is moreover apparent in FIG. 8G, the remaining surface of the side 4 is unstructured and thus smoothly formed.

Figure 8E:
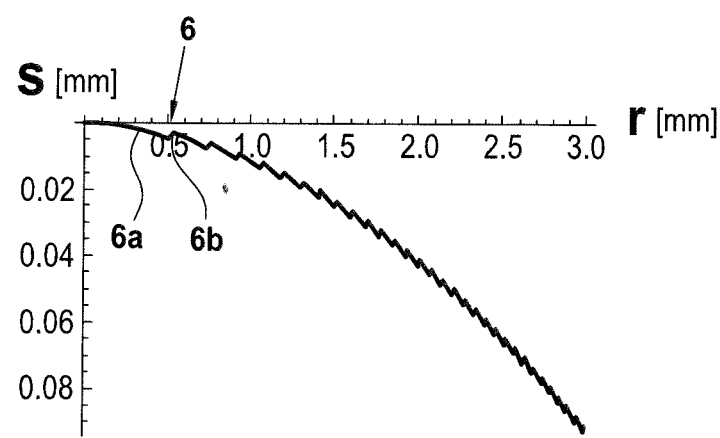
Figure 8G:
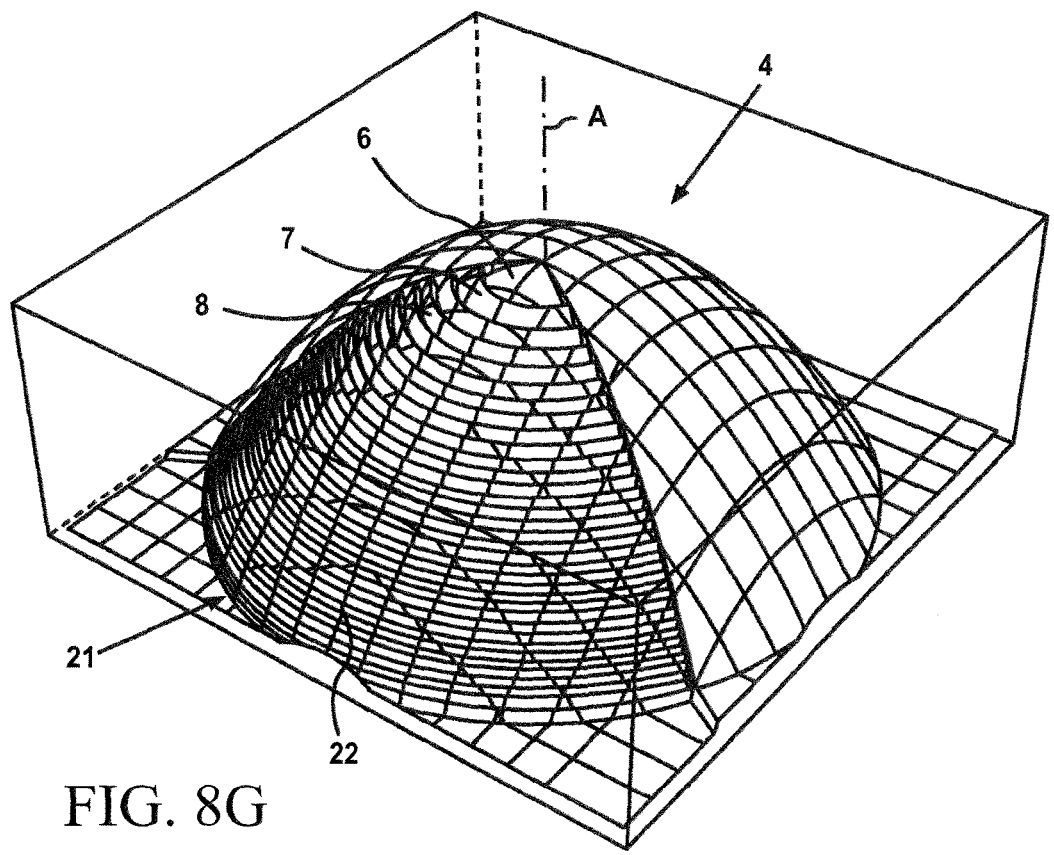

In FIG. 8E, a sectional representation of the topography in FIG. 8G is shown, wherein the sagittal height is therein shown depending on the radius and therein extends along the radius 22. Here too, the zones are formed with each one main sub-zone and one phase sub-zone, wherein only the innermost zone 6 with the main sub-zone 6a and the phase sub-zone 6b is represented in FIG. 8A.

In FIGS. 8B to 8G, specific parameters with their characteristic courses over the azimuth are again illustrated.

Figure 8F:
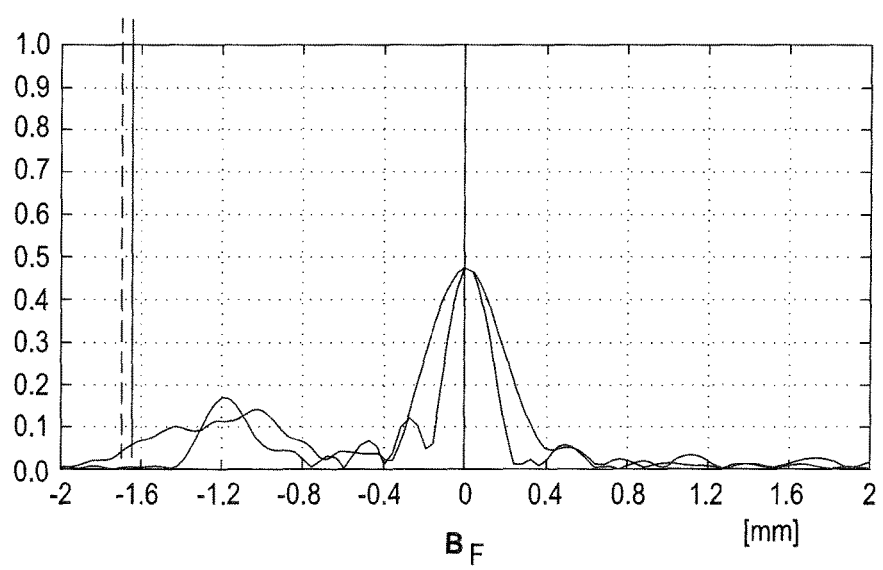

In FIG. 8F, the focus widening $B_F$ of the embodiment is again shown with respect to a configuration without such a variation of the phase deviation. Here too, the two foci are increased in their width such that increased depth of focus is also present in the respective foci.

By the ratio formation between the angular interval, in which the phase deviation is 0, and in which the phase deviation is >0, the intensity distribution between the far focus and the near focus can also be adjusted. The near focus is in particular characterized by the area, in which the phase deviation is Φ>0, and thus is characterized by the surface sector 22 in the shape of a spherical surface wedge.

In the embodiment according to FIGS. 9A to 9H, an eye lens 1 is exemplarily shown, in which a toric refractive surface shape 16 is additionally also formed besides a variation of the phase deviation ϕ to the annular zones.

Figure 9E:
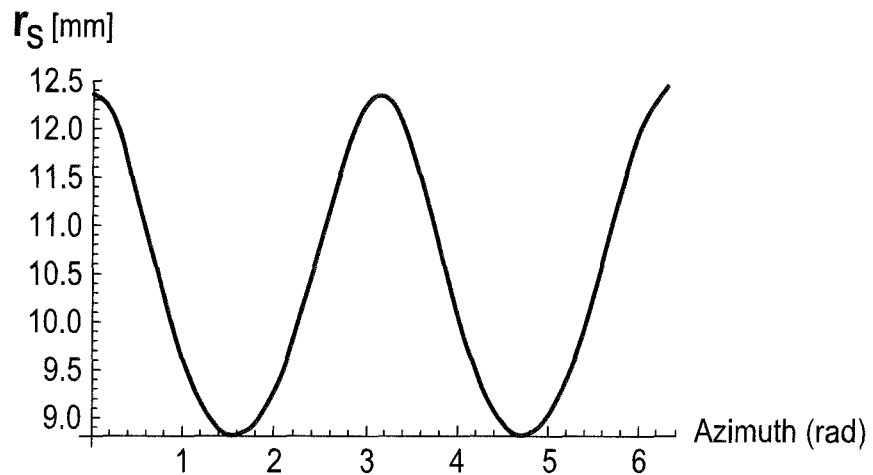
Figure 9F:
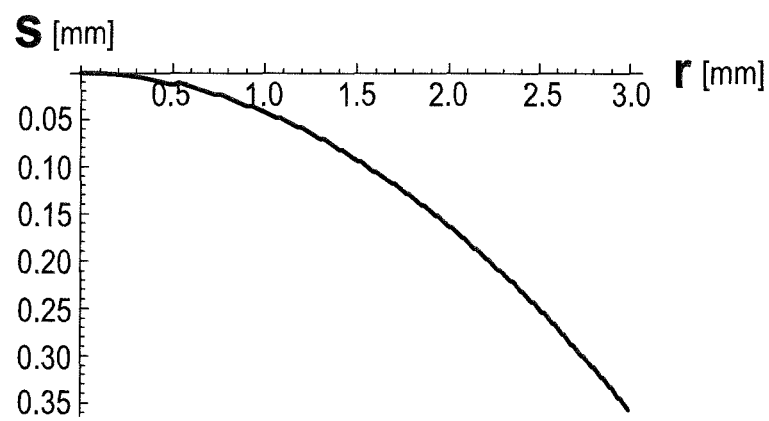
Figure 9G:
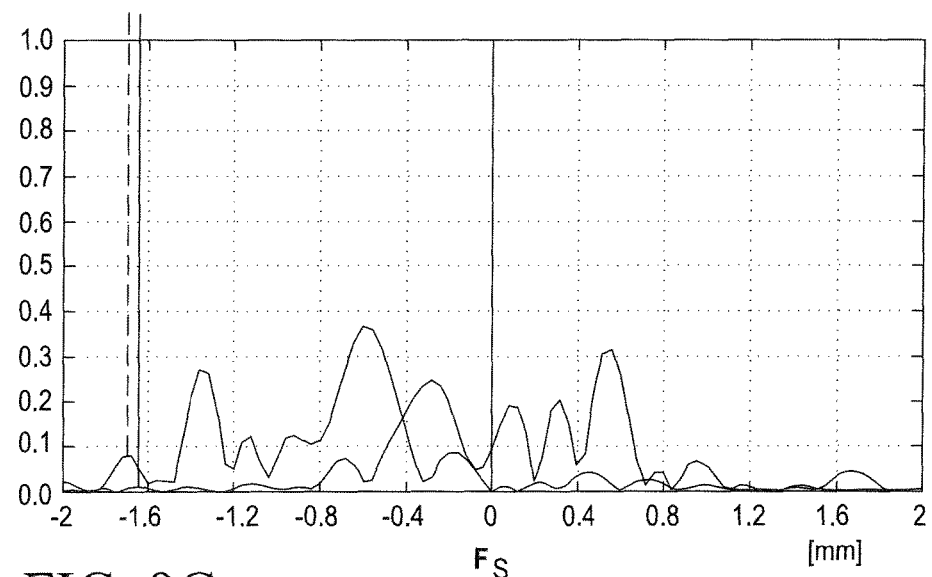
Figure 9H:
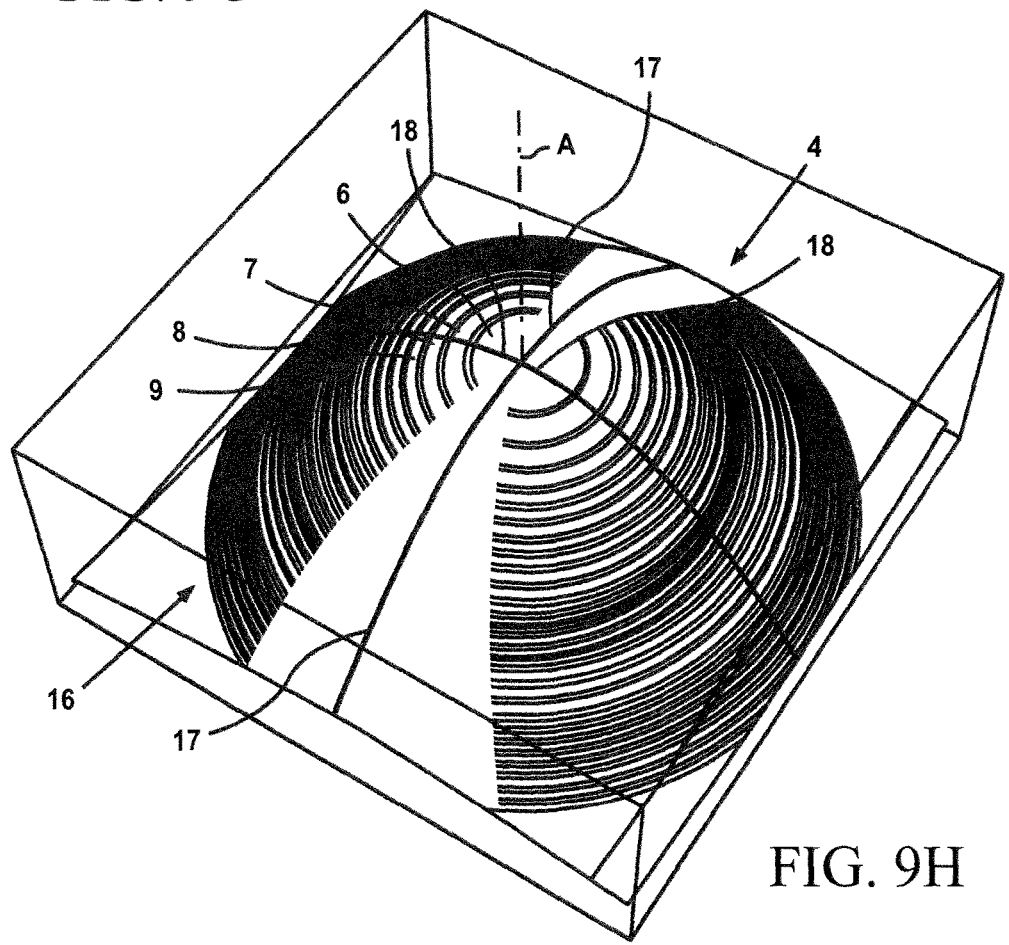

As is shown by the exemplary parameter values and the exemplary courses of the parameters depending on the azimuth in FIGS. 9A to 9F, a very specific surface topography, as it is three-dimensionally shown in FIG. 9H, is here achieved. The cylindrical refractive power, as it is contributed to the overall refractive power by the toric refractive surface shape 16 according to the course in FIG. 9C, and/or by the synchronous curve course of the phase deviation, as it is illustrated in FIG. 9D, the specific refractive power course of the overall refractive power in FIG. 9B is achieved. In particular, in this embodiment, the phase deviation is equal to 0 in the area of the main meridian 17, which represents the flatter main meridian. Thus, at this place, the topography is smooth and structures with respect to the zones then only correspondingly thereto clockwise and counter-clockwise.

Figure 10E:
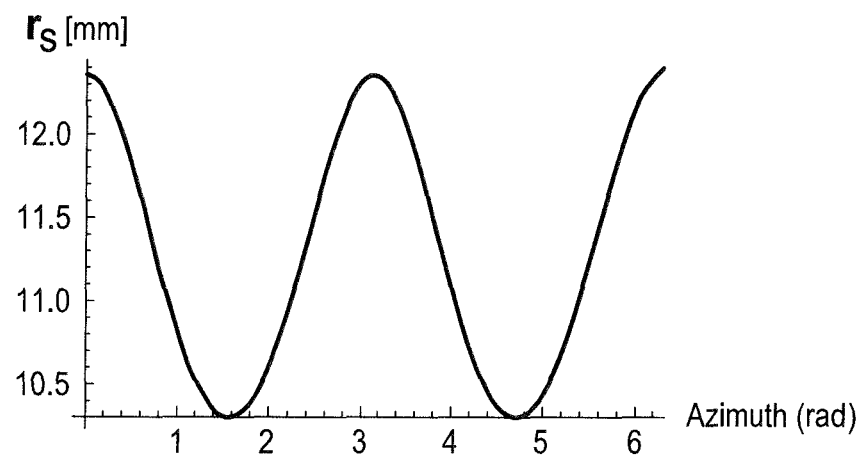
Figure 10F:
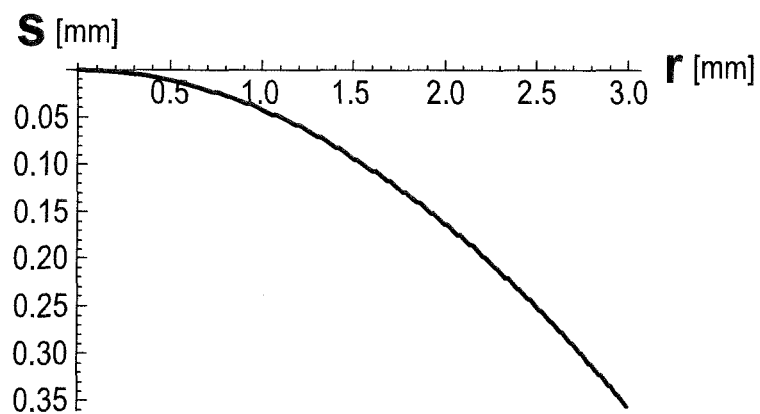
Figure 10G:
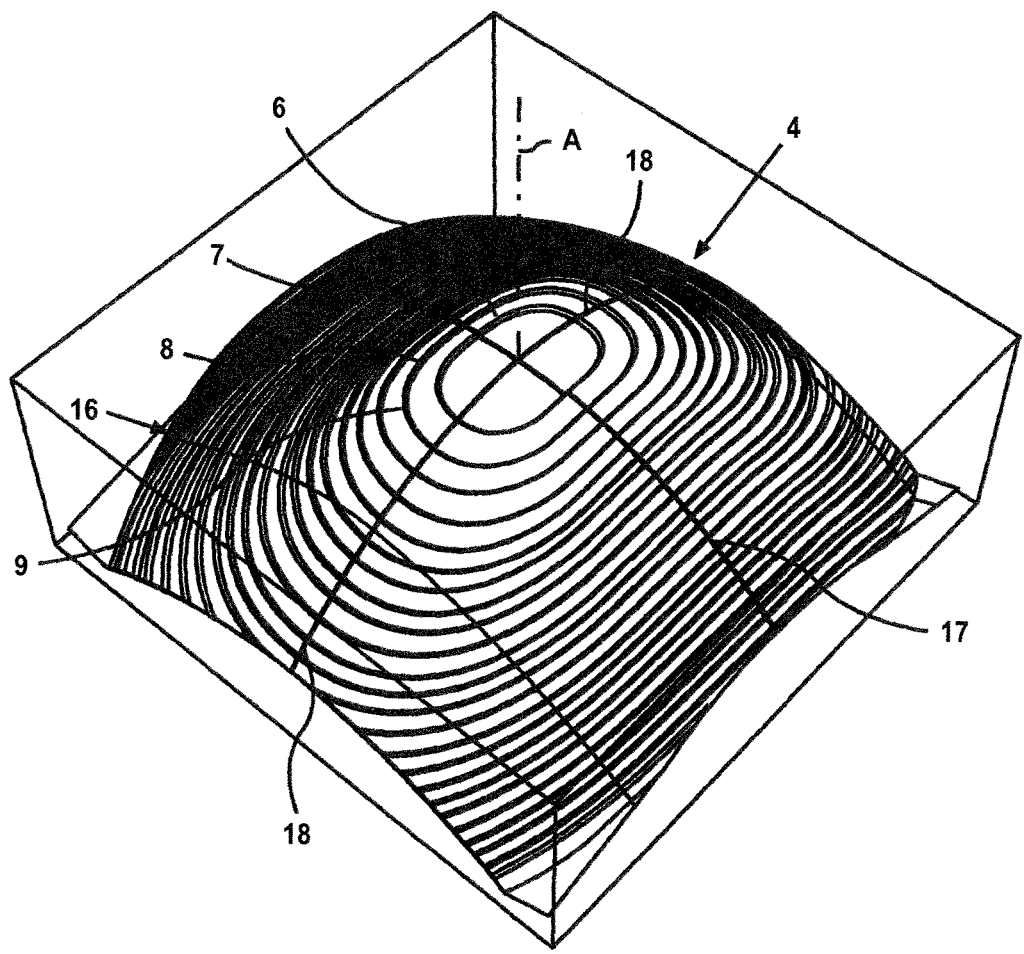

In FIGS. 10A to 10G, a further embodiment is shown, in which analogous to the configuration in FIGS. 9A to 9H, an azimuthal variation of the phase deviation is also effected besides the configurations of an annular zone with each one main sub-zone and one phase sub-zone and moreover a toric refractive surface shape 16 is superimposed, as it is illustrated in FIG. 10G.

A helix winding is not formed here too, but can also be provided superimposed both here and in the embodiment according to FIGS. 9A to 9H.

In this configuration, a relatively small phase deviation ϕ is again realized in azimuthal direction, as it is also illustrated in the diagram according to FIG. 10G. The course of the overall refractive power depending on the azimuth is illustrated in FIG. 10B.

In FIG. 10C, the azimuthal course of the normalization radius for the diffractive structure is shown, which exemplarily has a course with valleys and peaks.

The minimum standard radius rmmin is here 3 mm and the maximum standard radius rmmax is here 4.5 mm.

Thereby, the toric refractive surface shape 16 is also characterized.

By the main meridian 17, the flatter main meridian is shown, wherein the main meridian 18 perpendicular thereto represents the steeper one.

In the further diagrams according to FIGS. 10E and 10F, the apex radius of curvature for the sagittal height is represented depending on the azimuth and the radius, respectively.

In the embodiment according to FIGS. 11A to 11H, an eye lens is illustrated, in which the phase deviation again varies in azimuthal direction. Moreover, a helix winding and either a toric refractive surface shape are not configured here. However, it is provided here that the radius of the annular zones varies at least once in azimuthal direction.

Figure 11D:
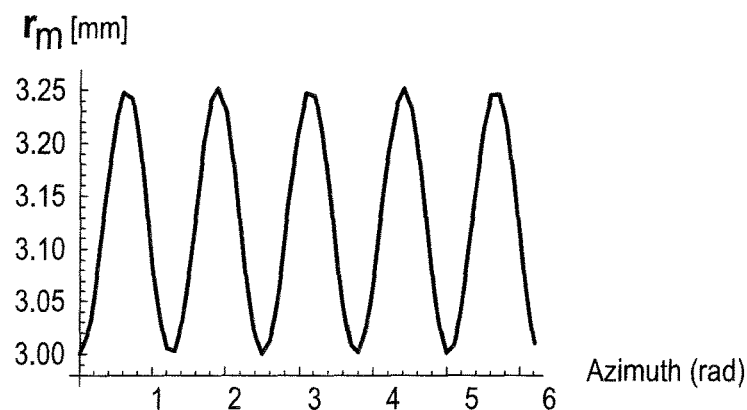
Figure 11E:
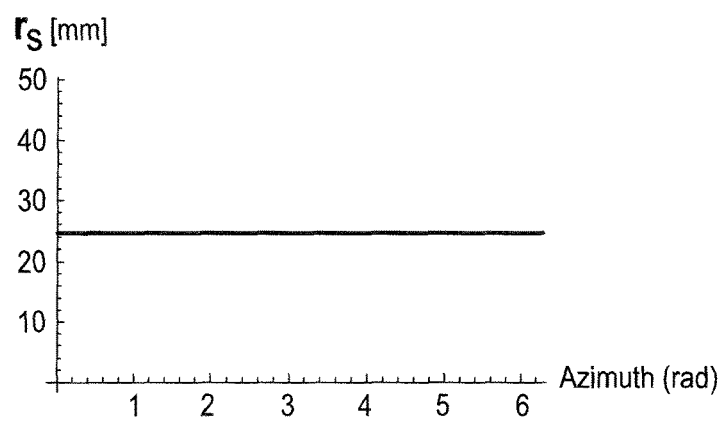
Figure 11F:
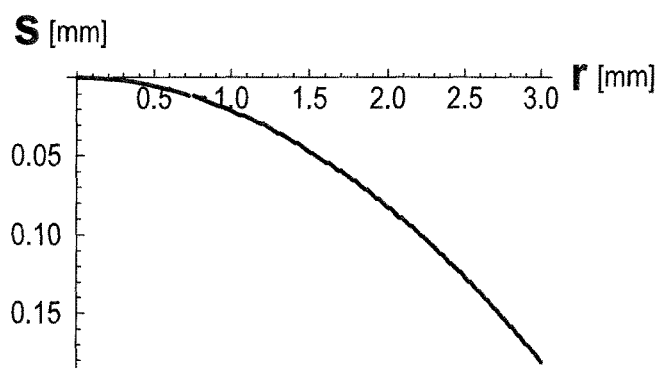

In FIG. 11A, therein, an exemplary parameter value set for an embodiment is again indicated. In the diagrams according to FIGS. 11A to 11F, specific parameters depending on the azimuth and on the radius, respectively, are again illustrated. In particular in FIG. 11D, the azimuthal radius variation is shown in this context, which here symmetrically resembles a curve course with valleys and peaks. This course is to be taken as a basis for the at least inner zones in the embodiment such that they have the respective different radii in radial direction respectively in the same azimuthal position.

Figure 11G:
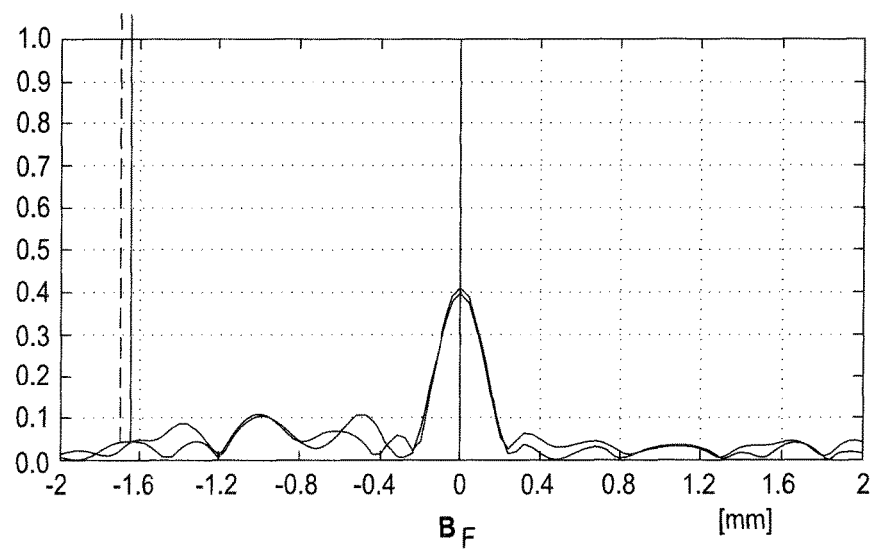

In FIG. 11G, the width of the foci of the lens is again shown.

Figure 11H:
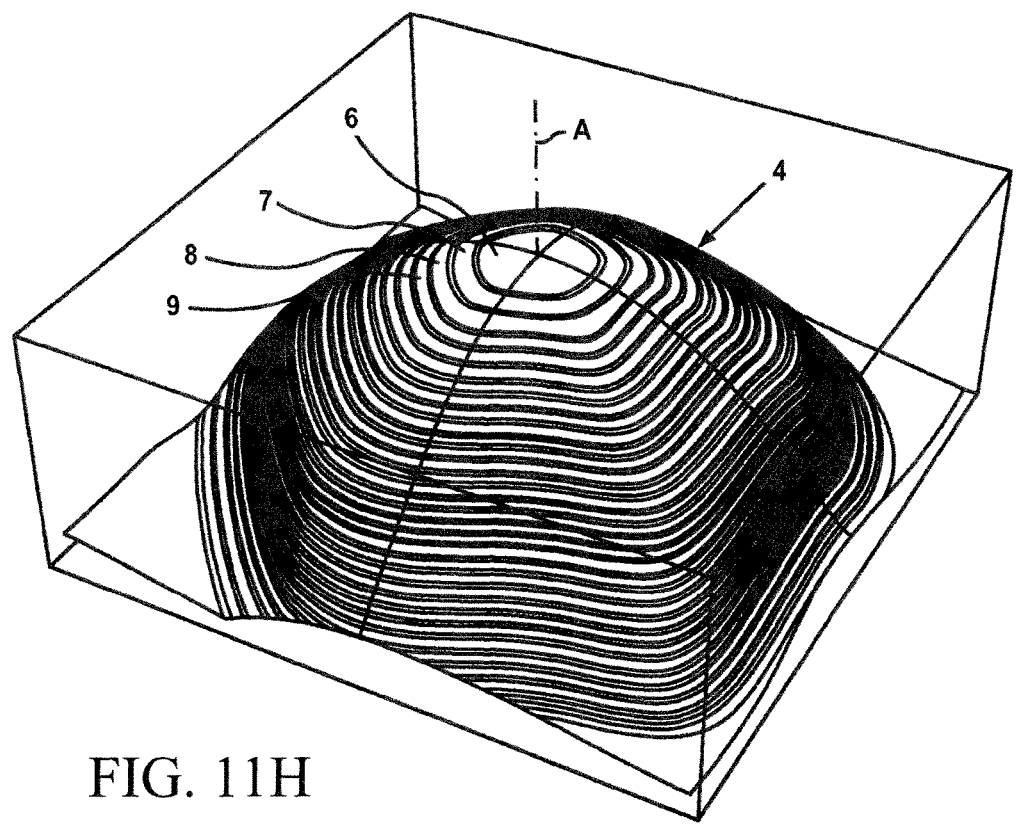

In the three-dimensional image in FIG. 11H, the surface topography of the embodiment is shown. The course of the individual zones in azimuthal direction is apparent, wherein this is configured with a view along the axis A such that these zones 6 to 9 are configured similar to a polygon ring. In the shown embodiment, a helix winding and a toric refractive surface shape are not formed or superimposed.

However, here too, it can be provided that a toric refractive surface shape is also present, for example with a refractive power portion between 1 diopter and 3 diopters, in particular 2 diopters.

These exemplary values can also be formed in the other implementations, which were explained without toric surface shape heretofore if a toric surface shape is additionally formed.

Figure 12E:
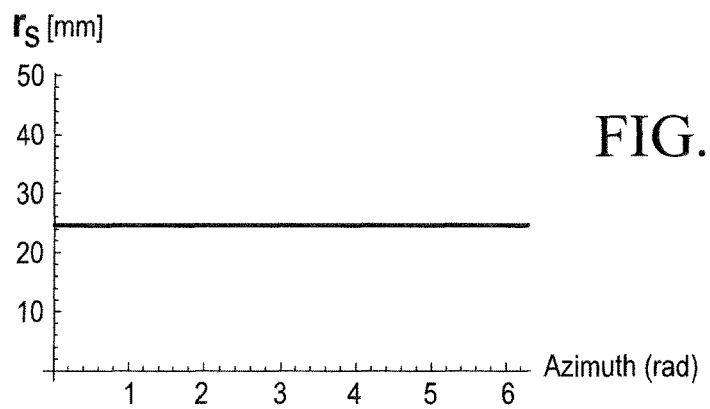
Figure 12F:
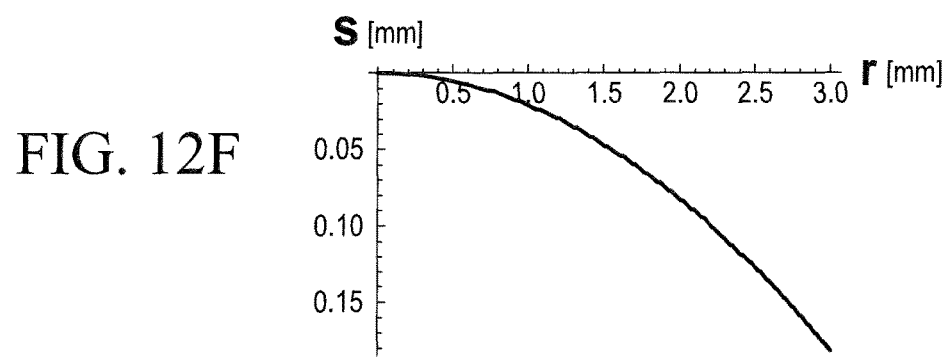

In FIGS. 12A to 12G, a further embodiment of an eye lens 1 is shown, in which the maximum standard radius rmmax is larger in contrast to the implementation in FIG. 11A. Moreover, the course of this normalization radius is illustrated in FIG. 12D, which does not have a course with multiple valleys and peaks, but is formed continuously increasing.

In FIGS. 12B, 12C, 12E and 12F, specific curve courses for specific parameters are again illustrated depending on the azimuth and the radius, respectively.

Figure 12G:
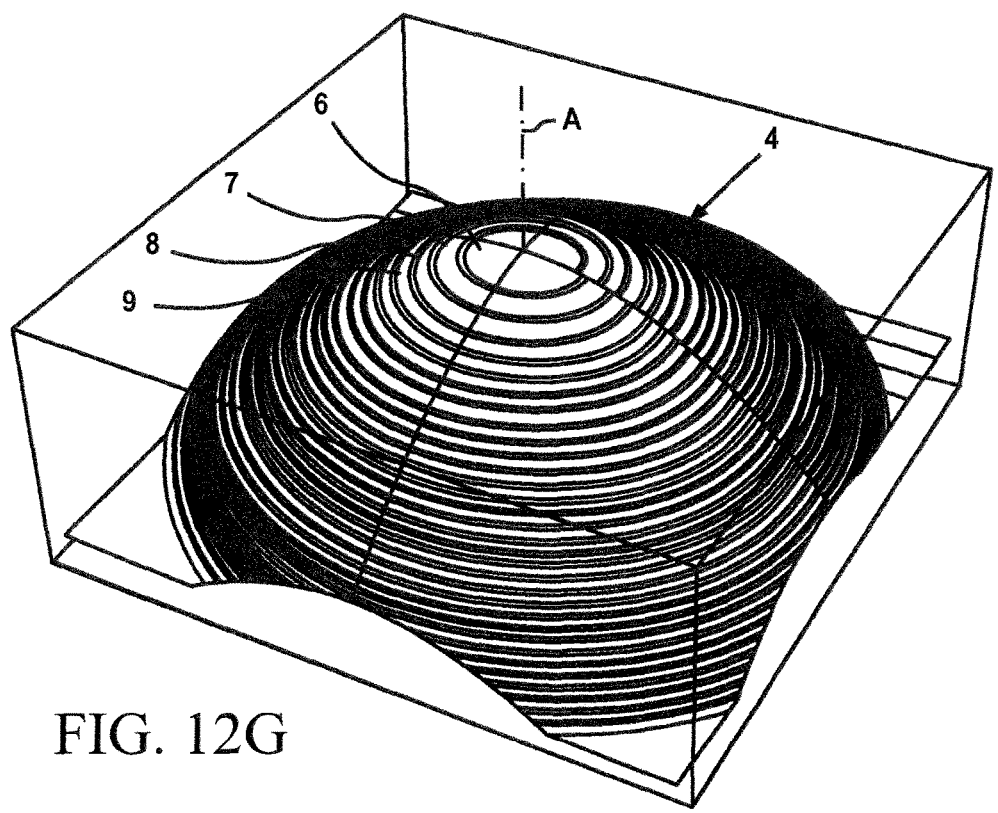

In FIG. 12G, the three-dimensional surface topography to this embodiment is exemplarily and schematically shown.

Figure 13E:
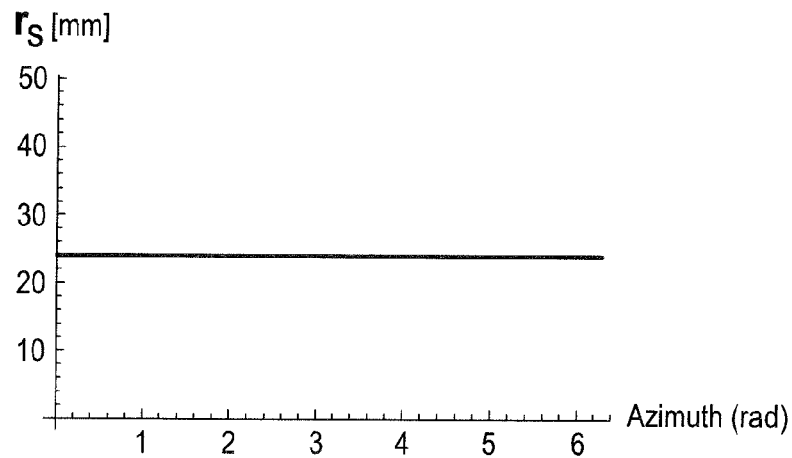
Figure 13F:
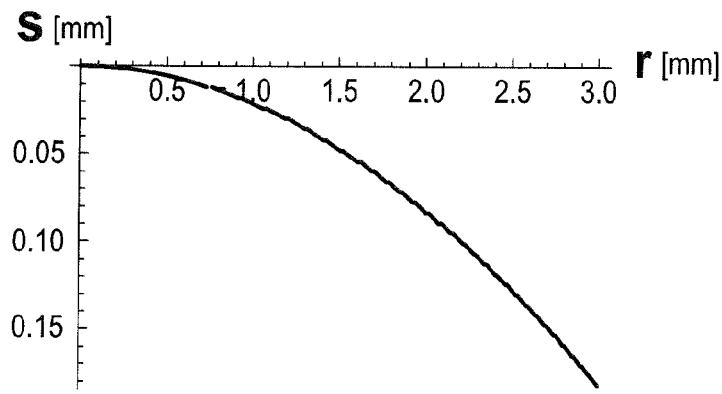
Figure 13G:
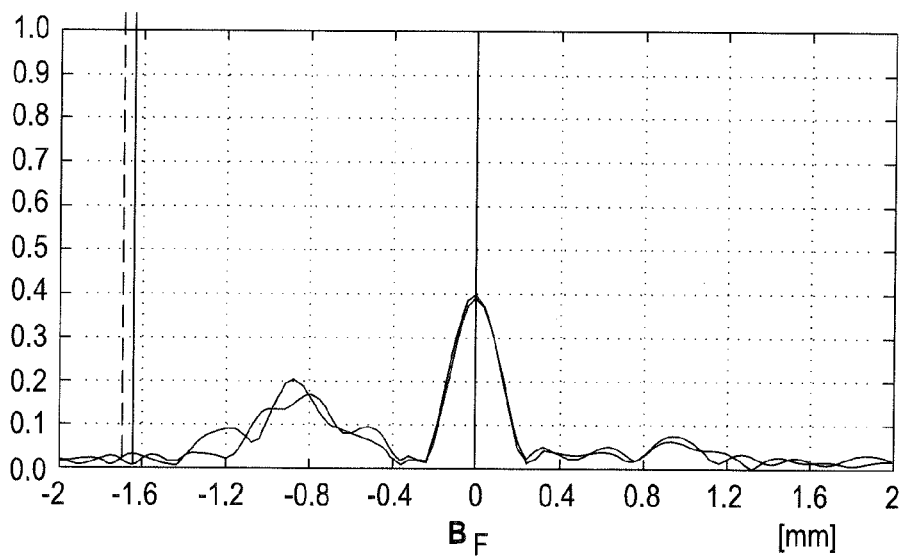
Figure 14E:
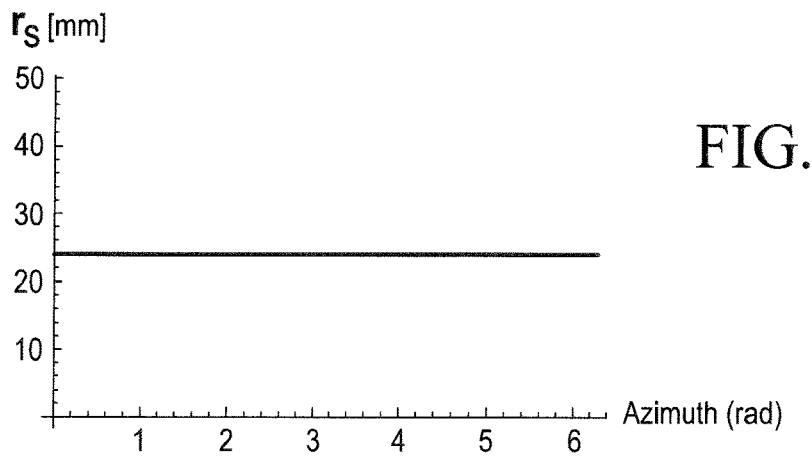
Figure 14F:
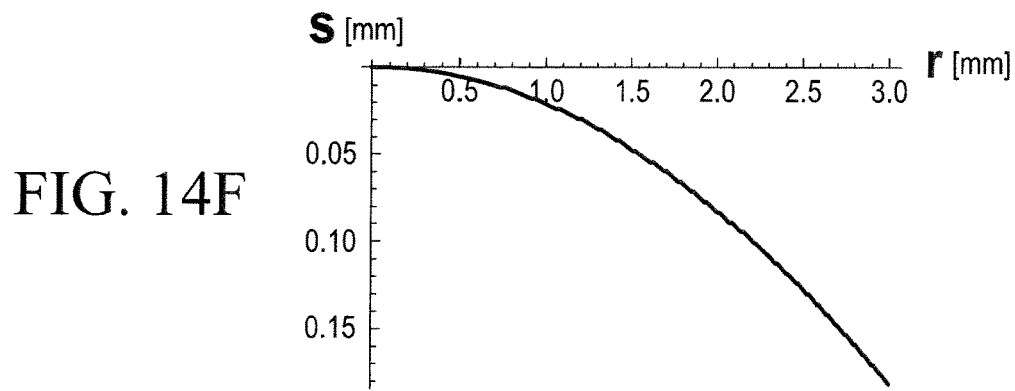
Figure 14G:
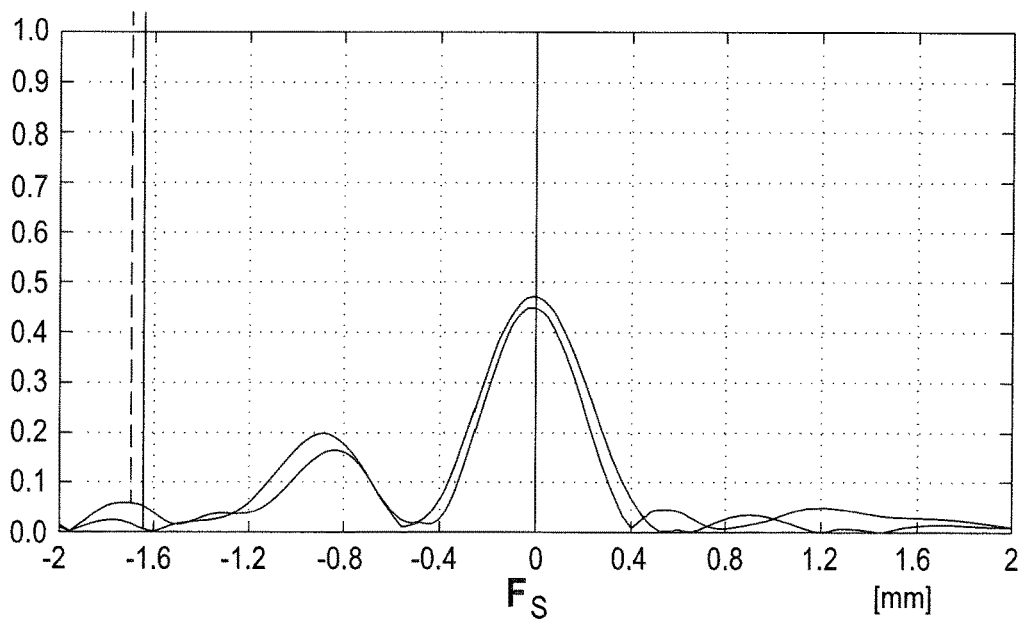
Figure 14H:
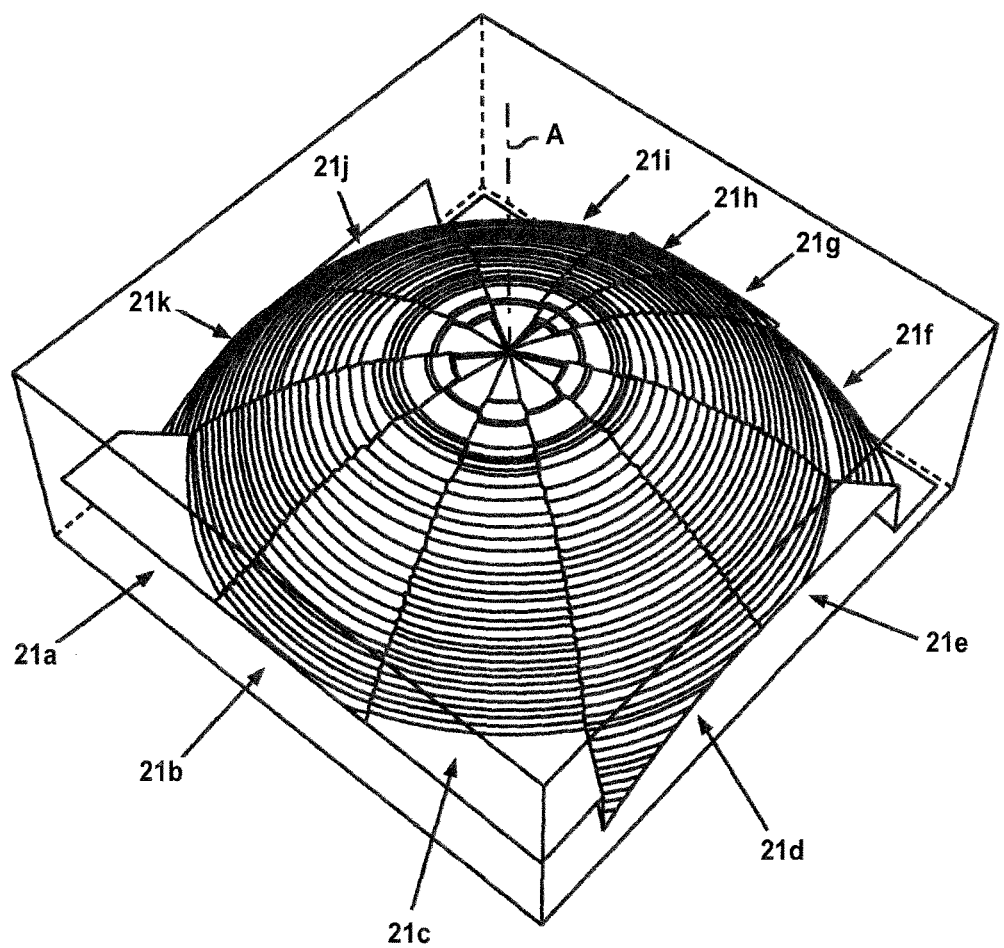

In the embodiment in FIGS. 13A to 13G, in contrast to the implementations in FIGS. 11A to 11H and 12A to 12G, the maximum normalization radius rmmax is again increased and the azimuthal curve course according to the representation in FIG. 13C is similar to the course in FIG. 12D. The further diagrams then again show representations of specific parameters depending on the azimuth and the radius, respectively, here too, as well as the representation of the focus width.

A final example is illustrated in FIGS. 14A to 14H. In this implementation, an azimuthal variation of the phase deviation φ is again provided. Besides the annular zones, which here too again for example each have a main sub-zone and a phase sub-zone, a helix winding and either a toric refractive surface shape are not provided as additional structure contributing to the optical imaging characteristic. However, it can also be provided here too that a helix winding once encircling the optical axis A and/or a toric refractive surface shape are formed or superimposed.

In this embodiment, according to the representation in FIG. 14B, a constant course of the overall refractive power depending on the azimuth is also again represented.

Here, the course of the normalization radius, as it is shown in FIG. 14C, is very specific, namely by a stepped discrete profile. The multiple stepping results in the fact that according to the three-dimensional representation of the surface topography in FIG. 14H, multiple surface sectors 21a, 21b, 21c, 21d, 21e, 21f, 21g, 21h, 21i, 21j and 21k in the shape of a spherical surface wedge are formed. According to the specific course specification, as it is shown in FIG. 14C, these surface sectors 21a to 21k each extend over a same azimuthal angular range. Moreover, in particular these surface sectors 21a to 21k are different in the number of the respectively radially formed zones and/or the radial width of these zones and/or the area sizes of these zones and/or the phase deviations of these zones. In particular, this is also shown with regard to the phase deviation by the course in FIG. 14D.

Thus, by this specific configuration, extremely individual surface topographies for eye lenses can be generated, which can be configured in sectorially individual manner and in particular also independently of other sectors. Thereby, very individual imaging characteristics can be achieved.

In all of the explained embodiments with the specific numerical values, it can also be provided that at least one parameter value of a parameter is respectively varied and/or at least one curve course of a parameter is otherwise configured. In the individual specifically explained embodiments, the zone configurations with respect to the number of the main sub-zones and/or the number of the phase sub-zones and/or with respect to the area portions of a main sub-zone and/or a phase zone can also be different. Similarly, it can be provided that in implementations, which do not have a helix winding, such a helix winding is also formed. Similarly, in implementations, which do not have a toric refractive surface shape, such one can also be formed. Similarly, in implementations, in which the phase deviation is constant in azimuthal direction, a variation in azimuthal direction can be present. Thus, a plurality of further embodiments is also to be considered as disclosed, which arise from the explained embodiments by the above mentioned variations of parameters and/or surface topographies.

Very generally, it is also to be mentioned that in all of the embodiments, a division of a partial profile contributing to the overall refractive power of the eye lens can also be distributed to both sides 4 and 5 and/or the respective profiles can be formed on different sides 4 and 5.

It is understood that the foregoing description is that of the preferred embodiments of the invention and that various changes and modifications may be made thereto without departing from the spirit and scope of the invention as defined in the appended claims.

What is claimed is:

1. A multifocal eye lens defining a main optical axis, the multifocal eye lens comprising:
    an optical part, viewed in the direction of said main optical axis (A), having a first optical side and a second optical side disposed opposite to said first optical side;
    a plurality of annular optical zones formed on at least one of said first and said second optical sides;
    said annular optical zones at least partially encircling said main optical axis (A);
    at least a portion of said annular optical zones each including at least one main sub-zone;
    a helix winding formed on at least one of said first and said second optical side and configured, in addition to said annular optical zones, as a surface structure of said optical part;

said helix winding running in an encircling direction about said main optical axis (A);

the lens having a refractive power varying in value imparted thereto via said helix winding running in said circumferential direction;

said portion of said annular optical zones each further including a phase sub-zone;

the lens having an overall refractive power; and, further including at least one of (a) and (b):

(a) each of said main sub-zones of said portion of said annular optical zones has a main sub-zone refractive power contributing to said overall refractive power of the lens varying at least once in azimuthal direction around said main optical axis (A); and, (b) each of said phase sub-zones of said portion of said annular optical zones has a sub-zone refractive power contributing to said overall refractive power of the lens varying at least once in azimuthal direction around said main optical axis (A).

2. The multifocal eye lens of claim 1, wherein said annular optical zones and said helix winding are formed or superimposed on a common one of said first and said second optical sides.

3. The multifocal eye lens of claim 1, wherein said plurality of annular optical zones are formed on said first optical side and said helix winding is formed on said second optical side.

4. The multifocal eye lens of claim 1, wherein:

each one of said portion of said annular optical zones has an overall area; and, said main sub-zone of each one of said portion of said annular optical zones has a main sub-zone area of at least 80% of the corresponding one of said overall areas.

5. The multifocal eye lens of claim 1, wherein a phase deviation ($\Phi$) between two mutually adjacent ones of said annular optical zones is in an interval of $<\lambda$.

6. The multifocal eye lens of claim 5, wherein at least one annular optical zone has a phase deviation ($\Phi$) which is constant in the azimuthal direction around the main optical axis (A).

7. The multifocal eye lens of claim 5, wherein at least one annular optical zone has a phase deviation ($\Phi$) which varies in the azimuthal direction around the main optical axis (A).

8. The multifocal eye lens of claim 7, wherein said phase deviation ($\Phi$) of said at least one optical zone is steplessly varied.

9. The multifocal eye lens of claim 7, wherein said phase deviation ($\Phi$) of said at least one optical zone is varied at least once by a discrete phase deviation step.

10. The multifocal eye lens of claim 7, wherein:

said interval includes a first partial azimuthal interval in which said phase deviation ($\Phi$) is equal to zero and a second partial azimuthal interval in which said phase deviation ($\Phi$) is unequal to zero;

the lens has a near refractive power and a far refractive power defining a ratio therebetween; and, said ratio between said near refractive power and said far refractive power of the lens is variable in dependence upon a ratio between said first and said second partial azimuthal intervals.

11. The multifocal eye lens of claim 1, wherein a phase deviation ($\Phi$) between two mutually adjacent ones of said annular optical zones is in an interval of $0.3\lambda \leq \Phi(\alpha) \leq 0.6\lambda$.

12. The multifocal eye lens of claim 1, wherein:

said helix winding has a winding start and a winding end; and, said helix winding is formed once encircling the main optical axis (A) and has a stepped transition formed between said winding start and said winding end.

13. The multifocal eye lens of claim 1, wherein the eye lens, in addition to said annular optical zones and said helix winding, has a toric refractive surface shape and said toric refractive surface shape is formed on at least one of said first optical side and said second optical side.

14. The multifocal eye lens of claim 13, wherein:

said toric refractive surface shape has a flat main meridian;

said helix winding is formed once encircling the main optical axis (A) and has a stepped transition formed between said winding start and said winding end; and, said stepped transition is offset in azimuthal direction with respect to said flat main meridian.

15. The multifocal eye lens of claim 14, wherein said offset is between $(\frac{1}{4}\pi)+/-(\frac{1}{8}\pi)$ or $(\frac{5}{4}\pi)+/-(\frac{1}{8}\pi)$.

16. The multifocal eye lens of claim 13, wherein:

said toric refractive surface shape has a flat main meridian; and, said stepped transition is formed at an azimuthal angle between 20° and 70° or between 200° and 250° to said flat meridian of said toric refractive surface shape in azimuthal position around said main optical axis (A).

17. The multifocal eye lens of claim 13, wherein:

said toric refractive surface shape has a flat main meridian; and, said stepped transition is formed at an azimuthal angle between 40° and 50° or between 220° and 230° to said flat meridian of said toric refractive surface shape in azimuthal position around said main optical axis (A).

18. The multifocal eye lens of claim 1, wherein the lens has $n \geq 2$ foci and the helix winding is formed such that maximally $n-1$ foci are increased in the depth of focus by the helix winding.

19. A multifocal eye lens defining a main optical axis (A), the multifocal eye lens comprising:

an optical part, viewed in the direction of said main optical axis (A), having a first optical side and a second optical side disposed opposite to said first side;

a plurality of annular optical zones formed on at least one of said first and said second optical sides;

said annular optical zones at least partially encircling said main optical axis (A);

at least a portion of said annular optical zones each including at least one main sub-zone;

mutually adjacent ones of said annular optical zones having a phase deviation ($\Phi$) formed therebetween;

said phase deviation being varied in azimuthal direction between at least mutually adjacent ones of said annular optical zones;

said portion of said annular optical zones each further including a phase sub-zone;

the lens having an overall refractive power; and, further including at least one of (a) and (b):

(a) each of said main sub-zones of said portion of said annular optical zones has a main sub-zone refractive power contributing to said overall refractive power of the lens varying at least once in azimuthal direction around said main optical axis (A); and, (b) each of said phase sub-zones of said portion of said annular optical zones has a sub-zone refractive power contributing to said overall refractive power of the lens varying at least once in azimuthal direction around said main optical axis (A).

20. The multifocal eye lens of claim 19, wherein each of at least said portion of said annular optical zones has a radius and said radius of at least one of said portion of said annular optical zones is varied at least once in azimuthal direction around said main optical axis (A).

21. The multifocal eye lens of claim 20, wherein said radii of said portion of said annular optical zones are varied at least once and the azimuthal position of the variations is identical in said portion of annular optical zones.

22. The multifocal eye lens of claim 19, wherein:
- one of said first optical side and said second optical side has a first surface sector and at least a second surface sector formed thereon in azimuthal direction around said main optical axis (A);
- said first and said second surface sector have a shape of a spherical surface wedge; and,
- at least one of the number of zones and the area sizes of the zones are different between said first surface sector and said second surface sector.

23. A multifocal eye lens defining a main optical axis (A), the multifocal eye lens comprising:
- an optical part, viewed in the direction of said main optical axis (A), having a first optical side and a second optical side disposed opposite to said first side;
- a plurality of annular optical zones formed on at least one of said first and said second optical sides;
- said annular optical zones at least partially encircling said main optical axis (A);
- at least a portion of said annular optical zones each including at least one main sub-zone;
- two mutually adjacent ones of said annular optical zones having a phase deviation ($\Phi$) formed therebetween;
- the lens having an overall refractive power which is varied in increasing manner in azimuthal direction in a circulation about said main optical axis (A) without an intermediate minimum of said refractive power;
- said portion of said annular optical zones each further including a phase sub-zone;
- the lens having an overall refractive power; and,
- further including at least one of (a) and (b):
- (a) each of said main sub-zones of said portion of said annular optical zones has a main sub-zone refractive power contributing to said overall refractive power of the lens varying at least once in azimuthal direction around said main optical axis (A); and,
- (b) each of said phase sub-zones of said portion of said annular optical zones has a sub-zone refractive power contributing to said overall refractive power of the lens varying at least once in azimuthal direction around said main optical axis (A).

\* \* \* \* \*